United States Patent [19]

Lane et al.

[11] Patent Number: 5,401,631

[45] Date of Patent: Mar. 28, 1995

[54] UNIVERSAL EUBACTERIA NUCLEIC ACID PROBES AND ASSAY METHODS

[75] Inventors: David J. Lane, Milford, Mass.; Jyotsna Shah, Nashua, N.H.; Amelia Buharin, Framingham; William G. Weisburg, Milford, both of Mass.

[73] Assignee: Amoco Corporation, Naperville, Ill.

[21] Appl. No.: 767,022

[22] Filed: Sep. 27, 1991

Related U.S. Application Data

[63] Continuation of Ser. No. 359,158, May 31, 1989, abandoned.

[51] Int. Cl.$^6$ ............................................. C12Q 1/68
[52] U.S. Cl. ............................................. 435/6; 935/77; 935/78
[58] Field of Search ............... 435/6; 436/501; 536/27, 536/23.1, 24.32; 935/77–78

[56] References Cited

U.S. PATENT DOCUMENTS

4,851,330  7/1989  Kohne ............................. 435/6
5,334,501  8/1994  Adams et al. .................... 435/6

FOREIGN PATENT DOCUMENTS

8705907  10/1987  WIPO ............................. 435/6
8803957  6/1988  WIPO ............................. 435/6

OTHER PUBLICATIONS

Giovannoni et al., J. Bact. 170(2):720–726 (Feb., 1988).
Lane et al., PNAS (USA) 82:6955–6959 (Oct., 1985).
Carl R. Woese, "Bacterial Evolution," *Micro. Biol. Reviews*, 51:221–271 (1987).
David E. Kohne, "Isolation and Characterization of Bacterial Ribosomal RNA Cistrons," *BioPhysical Journal* 8: 1104–1118 (1968).
B. Pace and L. Leon Campbell, "Homology of Ribosomal Ribonucleic Acid of Diverse Bacterial Species with *Escherichia Coli* and Bacillus Stearothermophilus," *Journal of Bacteriology* 107: 543–547 (1971).
Delond et al., "Phylogenetic Stains: Ribosomal RNA-- Based Probes for the Identification of Single Cells," *Science*, 243: 1360 (1989).
Chen et al., "Broad Range DNA Probes for Detecting and Amplifying Eubacterial Nucleic Acids," *FEMS Microbiology letter*, 48: 19–24 (1989).
Giovannoni S. J. et al., "Phylogenetic Group-Specific Oligodeoxynucleotide Probes for Identification of Single Microbial Cells," *Journal of Bacteriology*, 170: 720–726 (1988).
Carl R. Woese, "Archaebacteria," *Scientific American* 244, Jun. Issue #6, 98–102 (1981).

*Primary Examiner*—Stephanie W. Zitomer
*Attorney, Agent, or Firm*—Norval B. Galloway

[57] ABSTRACT

Nucleic acid probes capable of hybridizing to rRNA of eubacteria and not to rRNA of non-eubacteria are described along with methods utilizing such probes for the detection of eubacteria in clinical and other samples. Preferred embodiments include probes capable of distinguishing between gram-positive and gram-negative bacteria.

3 Claims, 2 Drawing Sheets

UNIVERSAL EUBACTERIA NUCLEIC ACID PROBES AND ASSAY METHODS

This is a continuation of application Ser. No. 07/359,158, filed May 31, 1989, and now abandoned.

FIELD OF THE INVENTION

This invention relates to detection of bacteria in clinical and other samples. Methods for the detection of bacteria in ordinarily aseptic bodily tissues or fluids such as blood, urine, and cerebrospinal fluid fluid— where the presence of any bacterium may be life threatening are of particular importance. The present invention provides nucleic acid probes and compositions along with methods for their use for the specific detection of any bacterium in such samples.

BACKGROUND OF THE INVENTION

The term "eubacteria" as used herein, refers to the group of prokaryotic organisms (bacteria) as described in, for example, Bergey's Manual of Systematic Bacteriology (N. R. Krieg and J. G. Holt, ed., 1984, Williams & Wilkins, Baltimore). As a group, the eubacteria comprise all of the bacteria which are known to cause disease in humans or animals and are of most concern with respect to detection.

The only other described group of bacteria, the archaebacteria, are biologically and genetically distinct from the eubacteria (C. R. Woese, Scientific American, 1981, Volume 244, pages 98–102). Archaebacteria as a group occupy a variety of "extreme" environments such as hot springs, strongly oxygen-depleted muds, salt brines, etc., which generally do not support the growth of eubacteria. There are no known archaebacterial pathogens and, consequently, their detection is of little clinical significance.

Eukaryotic organisms comprise the third fundamental genetic lineage which, together with the eubacteria and archaebacteria, include all known life forms (FIG. 1). Eukaryotes include humans, animals, plants and a host of organizationally less complex, free-living and parasitic "protists," including: protozoans, fungi, ciliates, etc. In a clinical context, it is particularly important that eubacteria be distinguished from eukaryotic, e.g. fungal and protozoan, infections which may present the same symptoms but require a significantly different regime of antimicrobial or chemo-therapy. These genetic distinctions thus are clinically significant from the point of view of diagnosis and antimicrobial chemotherapy.

It is an aspect of the present invention to provide nucleic acid probes which discriminate between eubacterial, human (including human mitochondrial) and fungal rRNA molecules.

It is another aspect of the present invention to provide probes and probe sets which provide a basis for discriminating between Gram positive and Gram negative eubacteria.

Methods for detecting, identifying and enumerating bacteria in normally sterile body fluids vary with the type of sample and the suspected pathogen. No currently available method is optimal for the detection of all pathogens. Often a combination of methods must be used to increase the likelihood that the pathogen will be detected. All commonly used methods for detection of, for example, bacteremia or bacterial septicemia rely on the in vitro cultivation of microbes from clinical samples. Generally, a blood sample is drawn from a patient and incubated in a rich artificial culture medium and monitored for 1 to 14 days. During this time, the medium is examined or blindly sub-cultured (plated), or assayed chemically or isotopically for evidence of bacterial growth or fermentative processes. Clinicians generally draw two or three samples of 10 milliliters of blood which may yield as few as one to ten colony forming units of bacteria for a positive diagnosis. Following the isolation of individual colonies of bacteria on diagnostic solid media and/or by Gram-staining, presumptive identification of the bacteria (or fungus) is made.

All cultivation methods suffer a number of serious shortcomings, including the following:

High material costs;
Labor intensive;
Technologists extensively handle dangerous bodily fluids;
False positives due to handling;
False negatives due to low viable cell numbers;
False negatives due to fastidious media requirements of many potential pathogens; and
Relatively long time to positive diagnosis and identification.

Because of the relatively long time required by current methods to achieve a diagnosis and because of the potentially life threatening nature of such infections, antimicrobial therapy often is begun empirically before the results of such tests can be known.

Therefore, it is another aspect of the present invention to provide nucleic acid probes which are broadly specific for all eubacteria and which preferably do not react with other eukaryotic pathogens, especially fungi, which may be present in sampled materials.

It is yet another aspect of the present invention to provide probes which may be used in a variety of assay systems which avoid many of the disadvantages associated with traditional, multi-day culturing techniques.

It is still another aspect of the present invention to provide probes that are capable of hybridizing to the ribosomal ribonucleic acid (rRNA) of the targeted eubacterial organisms under normal assay conditions.

While Kohne et al. (Biophysical Journal 8:1104–1118, 1968) discuss one method for preparing probes to rRNA sequences, they do not provide the teaching necessary to make broad-specificity eubacterial probes.

Pace and Campbell (Journal of Bacteriology 107:543–547, 1971) discuss the homology of ribosomal ribonucleic acids from diverse bacterial species and a hybridization method for quantitating such homology levels. They do not identify particular nucleic acid sequences shared by bacteria, but absent in eukaryotes. Woese (Microbiological Reviews 51:221–271, 1987) describes the breadth of the eubacteria, in terms of rRNA sequence, but does not indicate sequences of interest for complete bacterial inclusivity. These references, however, fail to relieve the deficiency of Kohne's teaching with respect to eubacterial probes and, in particular, do not provide eubacterial specific probes useful in assays for detecting eubacteria in clinical or other samples.

Giovannoni et al. (Journal of Bacteriology 170:720–726, 1988) describe a number of probes which are claimed to be useful for the identification of broad groups of eubacteria, archaebacteria and eukaryotes. However, Giovannoni et al. do not disclose the probes of the present invention. Nor do they provide the teaching necessary to design such probes.

Hogan et al. (European patent publication WO 88/03957) describe a number of probes which are claimed to hybridize to a broad representation of eubacteria. However, Hogan et al. do not teach the probes of the present invention and also fail to relieve the deficiency of Kohne's teaching with respect to these probes.

Ribosomes are of profound importance to all organisms because they serve as the only means of translating genetic information into cellular proteins. A clear manifestation of this importance is the observation that all cells have ribosomes. Actively growing bacteria may have 20,000 or more ribosomes per cell. This makes ribosomes one of the most abundant macromolecular entities in a cell, and an attractive diagnostic assay target.

Ribosomes contain three distinct RNA molecules which in *Escherichia coli* are referred to as 5S, 16S and 23S rRNAs. These names historically are related to the size of the RNA molecules, as determined by their sedimentation rate. In actuality, however, ribosomal RNA molecules vary in size between organisms. Nonetheless, 5S, 16S and 23S rRNA are commonly used as generic names for the homologous RNA molecules in any bacteria, and this convention will be continued herein. Discussion will be confined to 16S and 23S rRNAs.

As used herein, probe(s) refer to synthetic or biologically produced nucleic acids (DNA or RNA) which, by design or selection, contain specific nucleotide sequences that allow them to hybridize under defined predetermined stringencies, specifically (i.e., preferentially, see below—Hybridization) to target nucleic acid sequences. In addition to their hybridization properties, probes also may contain certain constituents that pertain to their proper or optimal functioning under particular assay conditions. For example, probes may be modified to improve their resistance to nuclease degradation (e.g. by end capping), to carry detection ligands (e.g. fluorescein, 32-Phosphorous, biotin, etc.), or to facilitate their capture onto a solid support (e.g., poly-deoxyadenosine "tails"). Such modifications are elaborations on the basic probe function which is its ability to usefully discriminate between target and non-target organisms in a hybridization assay.

Hybridization traditionally is understood as the process by which, under predetermined reaction conditions, two partially or completely complementary strands of nucleic acid are allowed to come together in an antiparallel fashion (one oriented 5' to 3', the other 3' to 5') to form a double-stranded nucleic acid with specific and stable hydrogen bonds. (Note that nucleic acids do have a polarity; that is, one end of a nucleic acid strand is chemically different from another. This is defined by the polarity of the chemical linkages through the asymmetric sugar moiety of the nucleotide components. The terms 5' and 3' specifically refer to the ribose sugar carbons which bear those names. Except in rare or unusual circumstances, nucleic acid strands do not associate through hydrogen bonding of the base moieties in a parallel fashion. This concept is well understood by those skilled in the art.)

The stringency of a particular set of hybridization conditions is defined by the base composition of the probe/target duplex, as well as by the level and geometry of mispairing between the two nucleic acids.

Stringency may also be governed by such reaction parameters as the concentration and type of ionic species present in the hybridization solution, the types and concentrations of denaturing agents present, and/or the temperature of hybridization. Generally, as hybridization conditions become more stringent, longer probes are preferred if stable hybrids are to be formed. As a corollary, the stringency of the conditions under which a hybridization is to take place (e.g., based on the type of assay to be performed) will dictate certain characteristics of the preferred probes to be employed. Such relationships are well understood and can be readily manipulated by those skilled in the art.

As a general matter, dependent upon probe length, such persons understand stringent conditions to mean approximately 35° C.–65° C. in a salt solution of approximately 0.9 molar.

SUMMARY OF THE INVENTION

In accordance with the various principles and aspects of the present invention, there are provided nucleic acid probes and probe sets comprising deoxyribonucleic acid (DNA) or ribonucleic acid (RNA) sequences which hybridize, under specific conditions, to the ribosomal RNA molecules (rRNA), rRNA genes (rDNA), and certain amplification and in vitro transcription products thereof of eubacteria but which do not hybridize, under the same conditions, to the rRNA or rDNA of eukaryotic cells which may be present in test samples. In addition, certain of the probes and probe sets described herein may be used as primers for the specific amplification of eubacterial rRNA or rDNA sequences which may be present in a sample by such methods as the polymerase chain reaction (U.S. Pat. No. 4,683,202) or transcriptional amplification systems (e.g. TAS, Kwoh et al., 1989, Proceedings of the National Academy of Science 86:1173–1177).

The probes of the present invention advantageously provide the basis for development of valuable nucleic acid hybridization assays for the specific detection of eubacteria in clinical samples such as blood, urine, cerebrospinal fluid, biopsy, synovial fluid, or other tissue or fluid samples from humans or animals. The probes also provide the basis for testing, for example in quality control, substances that are presumed sterile, e.g., pharmaceuticals. The probes described herein are specifically complimentary to certain highly conserved bacterial 23S or 16S rRNA sequences.

The detection of bacteria by nucleic acid hybridization constitutes enhanced performance capability compared to the available culture-dependent tests for several reasons including:

a) increased sensitivity; i.e., the ability to detect said bacteria in a given sample more frequently;
b) potentially significant reductions in assay cost due to the use of inexpensive reagents and reduced labor;
c) accurate detection of even nutritionally fastidious strains of bacteria;
d) faster results because such tests do not require the isolation of the target bacterium from the sample prior to testing;
e) the ability to screen, in a batch mode, a large number of samples, and only culture those identified as "hybridization positive";
f) potential detection of phagocytized organisms eliminating the need for multiple, punctuated blood samples in order to sample the cyclical "window"

of viable organisms (which probably depends on host immunological cycles);

g) some reduction of technologist handling of potentially infectious body fluids;

h) the ability to detect very low numbers of targets by amplifying either the bacterial signal or target using in vitro nucleic acid amplification.

It has been discovered that other advantages incurred by directing the probes of the present invention against rRNA include the fact that the rRNAs detected constitute a significant component of cellular mass. Although estimates of cellular ribosome content vary, actively growing *Escherichia coli*, for example, may contain upwards of 50,000 ribosomes per cell, and therefore 50,000 copies of each of the rRNAs (present in a 1:1:1 stiochiometry in ribosomes). The abundance of ribosomes in other bacteria particularly under other, less favorable, metabolic conditions may be considerably lower. However, under any circumstances, rRNAs are among the most abundant cellular nucleic acids present in all cell types. In contrast, other potential cellular target molecules such as genes or RNA transcripts thereof, are less ideal since they are present in much lower abundance.

A further unexpected advantage is that the rRNAs (and the genes specifying them) appear not to be subject to lateral transfer between contemporary organisms. Thus, the rRNA primary structure provides an organism-specific molecular target, rather than a gene-specific target as would likely be the case, for example of a plasmid-borne gene or product thereof which may be subject to lateral transmission between contemporary organisms.

Additionally, the present invention provides probes to eubacterial rRNA target sequences which are sufficiently similar in most or all eubacteria tested that they can hybridize to the target region in such eubacteria. Advantageously, these same rRNA target sequences are sufficiently different in most non-eubacterial rRNAs that, under conditions where the probes hybridize to eubacterial rRNAs they do not hybridize to most non-eubacterial rRNAs. These probe characteristics are defined as inclusivity and exclusivity, respectively.

The discovery that probes could be generated with the extraordinary inclusivity and exclusivity characteristics of those of the present invention with respect to eubacteria was unpredictable and unexpected.

BRIEF DESCRIPTION OF THE FIGURES

Further understanding of the principles and aspects of the present invention may be made by reference to the tables wherein.

BRIEF DESCRIPTION OF THE TABLES

Figure 1:
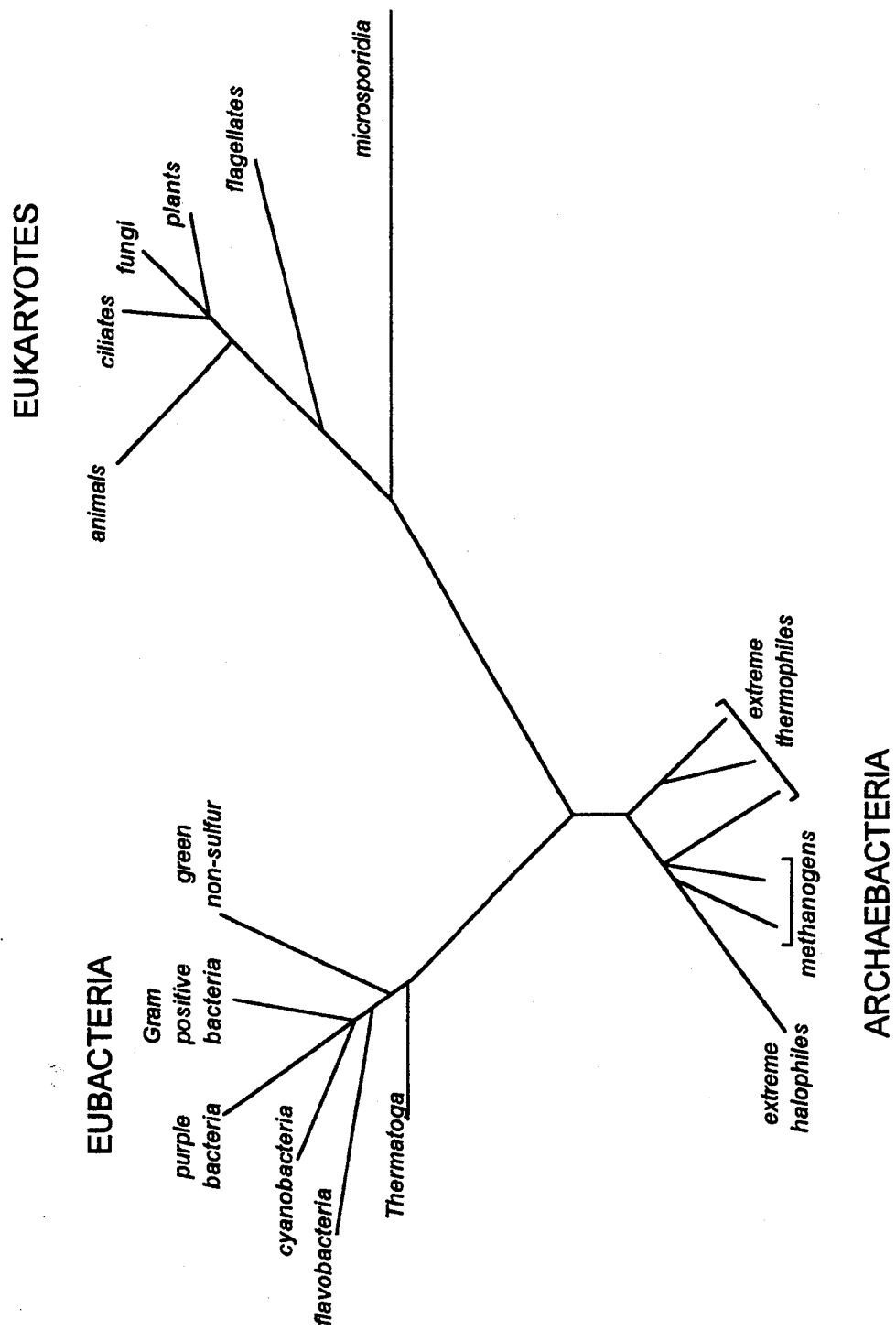
FIG. 1—Shows an evolutionary "tree" of the major genetic "kingdoms" of life (Woese, 1987, Microbiological Reviews 51:221-271). The branching patterns represent the mutational distances between the 16S rRNA sequences of the represented organism. Such comparisons readily distinguish the eubacteria from the archaebacteria and eukaryotes.

Table 1—Shows alignment of the nucleotide sequences of the preferred 16S rRNA-targeted probes of the present invention with their target nucleotide sequences in *E. coli* 16S rRNA. Very extensive sequence comparison to some 350 aligned 16S and 18S rRNA sequences were performed during the development of the probes of the present invention. It simply is not practical to show this analysis in detail. However, a consensus sequence (CONS-90%) of highly conserved 16S rRNA nucleotide positions is provided as a summary of the patterns of nucleotide sequence variation discovered among representative eubacteria. A nucleotide on the CONS-90% line indicates that nucleotide is found at the homologous position in 90% or greater of the eubacterial sequences inspected. Note that the probe target regions all correspond to clusters of high sequence conservation among the eubacterial 16S and 23S rRNA molecules.

Since the *E. coli* 16S and 23S rRNA sequences were among the first full rRNA sequences obtained, the assigned position numbers have become a convenient and commonly accepted standard for explicitly identifying the homologous regions in other rRNA sequences under consideration. In Table 1, the *E. coli* RNA (target) sequence is written 5' to 3'. Probe sequences are DNA and written 3' to 5', except for probes 1638, 1642 and 1643 which are designed to hybridize to the rRNA-complementary sequence rather than the rRNA itself. These latter probes have the same "sense" (i.e. polarity) as the rRNA and are written 5' to 3'.

Table 2—Shows alignment of the nucleotide sequences of the preferred 23S rRNA-targeted probes of the present invention with their target nucleotide sequences in *E. coli* 23S rRNA. As in Table 1 the *E. coli* sequence numbering is used as a standard in order to identify the homologous probe target sequences in all 23S rRNAs. CONS-90% has the same meaning as in TABLE 1. For the 23S rRNA analyses only about 30 sequences were available. However, these represent most of the major eubacterial divisions shown in FIG. 2. In the probe 1730 sequence, "R"=a 1:1 mixture of A and G at that position.

Table 3—Exemplifies the inclusivity and exclusivity behavior of a number of the preferred 16S rRNA-targeted probes toward a representative sampling of eubacterial and non-eubacterial rRNAs in a dot blot hybridization assay.

Table 4—Exemplifies the inclusivity and exclusivity behavior of a number of the preferred 23S rRNA-targeted probes toward a representative sampling of eubacterial and non-eubacterial rRNAs in a dot blot hybridization assay.

Table 5—Exemplifies the inclusivity and exclusivity behavior of a number of additional preferred 16S and 23S rRNA-targeted probes toward a representative sampling of eubacterial and non-eubacterial rRNAs in a dot blot hybridization assay. These probes exhibit useful patterns of hybridization to specific subgroups of eubacteria—notably Gram positive and Gram negative bacteria.

DETAILED DESCRIPTION OF THE INVENTION AND BEST MODE

Probe Development Strategy:

The first step taken in the development of the probes of the present invention involved identification of regions of 16S and 23S rRNA which potentially could serve as target sites for eubacteria specific nucleic acid probes. This entailed finding sites which are:

1) highly conserved (few nucleotide changes, deletions, or insertions) among eubacterial rRNA sequences, and
2) substantially different in non-eubacterial rRNA sequences.

For this analysis, precise alignments of available 16S and 23S rRNA sequences were developed. A number of 16S and 23S rRNA sequences were determined as part of this effort. Such nucleotide sequences were determined by standard laboratory protocols either by cloning (Maniatis et al., 1982, Molecular Cloning; A Laboratory Manual, Cold Spring Harbor Laboratory, New York, pp 545) and sequencing (Maxam and Gilbert, 1977, Proceedings of the National Academy of Science, USA 74:560–564; Sanger et al., 1977, Proceedings of the National Academy of Science; USA 74:5463–5467) the genes which specify the rRNAs, and/or by direct sequencing of the rRNAs themselves using reverse transcriptase (Lane et al., 1985, Proceedings of the National Academy of Science, USA 82:6955–6959; Lane, manuscript in preparation).

A computer algorithm, operating on the aligned set of 16S and 23S rRNA sequences, was used to identify regions of greatest similarity among eubacteria. Nucleic acid probes to such regions will hybridize most widely among diverse eubacteria.

Such regions of homology among eubacteria next were assessed for differences with non-eubacterial rRNA sequences. In particular, sequence differences between eubacterial and human, fungal, and mitochondrial sequences were sought.

Forty one probes were designed based on these analyses; 22 targeting 23S rRNA and 19 targeting 16S rRNA.

The hybridization behavior of these probes toward extensive panels of eubacteria was determined by hybridization analysis in a dot blot format.

Physical Description of the Probes:

The foregoing probe selection strategy yielded a number of probes useful for identifying eubacteria in samples and include the following preferred oligonucleotide probes:

16S rRNA-targeted probes:

Probe 1638: 5'-AGAGTTTGATCCTGGCTCAG-3'
Probe 1642: 5'-AGAGTTTGATCATGGCTCAG-3'
Probe 1643: 5'-AGAGTTTGATCCTGGCTTAG-3'
Probe 1738: 5'-CTGAGCCAGGATCAAACTCT-3'
Probe 1744: 5'-CAGCGTTCGTCCTGAGCCAGGATCAAACT-3'
Probe 1659: 5'-CTGCTGCCTCCCGTAGGAGT-3'
Probe 1660: 5'-CTGCTGCCTCCCGTAGGAGTTTGGGCCGTGTCTCAGTTCCAGTGT-3'
Probe 1661: 5'-TATTACCGCGGCTGCTGGCACGGAGTTAGCCG-3'
Probe 1739: 5'-GCGTGGACTACCGGGGTATCTAATCCTGTTTGCTCCCCACGCTTTCG-3'
Probe 1740: 5'-GGGTTGCGCTCGTTGCGGGACTTAACCCGACATCTCACGGCACGAGCT GACGACAGCCATGCAT-3'
Probe 1741: 5'-CTCACGGCACGAGCTGACGACAGCCATGCAT-3'
Probe 1742: 5'-GGGTTGCGCTCGTTGCGGGACTTAACCCGACAT-3'
Probe 1745: 5'-AGCTGACGACAACCATGCACCACCTGT-3'
Probe 1746: 5'TCATAAGGGGCATGATGATTTGACGTCAT-3'
Probe 1743: 5'-GTACAAGGCCCGGGAACGTATTCACCG-3'
Probe 1637: 5'-AAGGAGGTGATCCAGCC-3'
Probe 1639: 5'-ACGGTTACCTTGTTACGACTT-3'
Probe 1640: 5'-ACGGCTACCTTGTTACGACTT-3'
Probe 1641: 5'-ACGGATACCTTGTTACGACTT-3'

23S rRNA-targeted probes:

Probe 1730: 5'-CTTTTCTCCTTTCCCTCRCGGTACTGGTTCRCTATCGGTC'3
Probe 1731: 5'-CTTTTCGCCTTTCCCTCGCGGTACTGGTTCGCTATCGGTC'3
Probe 1658: 5'-TCTTTAAAGGGTGGCTGCTTCTAAGCCAACATCCTGGTTG-3'
Probe 1656: 5'-CTACCTGTGTCGGTTTGCGGTACGGGC-3'
Probe 1657: 5'-GGTATTCTCTACCTGACCACCTGTGTCGGTTTGGGGTACG-3'
Probe 1653: 5'-CCTTCTCCCGAAGTTACGGGGGCATTTTGCCTAGTTCCTT-3'
Probe 1654: 5'-CCTTCTCCCGAAGTTACGGGGTCATTTTGCCGAGTTCCTT-3'
Probe 1655: 5'-CCTTCTCCCGAAGTTACGGCACCATTTTGCCGAGTTCCTT-3'
Probe 1651: 5'-CTCCTCTTAACCTTCCAGCACCGGGCAGGC-3'
Probe 1652: 5'-TTCGATCAGGGGCTTCGCTTGCGCTGACCCCATCAATTAA-3'
Probe 1512: 5'-TTAGGACCGTTATAGTTACGGCCGCCGTTTACTGGGGCTT-3'
Probe 1256: 5'-GGTCGGAACTTACCCGACAAGGAATTTCGCTACCTTAG-3'
Probe 1398: 5'-GGTCGGTATTTAACCGACAAGGAATTTCGCTACCTTAG-3'
Probe 1511: 5'-CGTGCGGGTCGGAACTTACCCGACAAGGAATTTCGCTACC3'
Probe 1595: 5'-CGATATGAACTCTTGGGCGGTATCAGCCTGTTATCCCCGG-3'
Probe 1600: 5'-CAGCCCCAGGATGAGATGAGCCGACATCGAGGTGCCAAAC-3'
Probe 1601: 5'-CAGCCCCAGGATGTGATGAGCCGACATCGAGGTGCCAAAC-3'
Probe 1602: 5'-CAGCCCCAGGATGCGATGAGCCGACATCGAGGTGCCAAAC-3'
Probe 1598: 5'-CGTACCGCTTTAAATGGCGAACAGCCATACCCTTGGGACC-3'
Probe 1599: 5'-CGTGCCGCTTTAATGGCGAACAGCCCAACCCTTGGGACC-3'
Probe 1596: 5'-GATAGGGACCGAACTGTCTCACGACGTTTTGAACCCAGCT-3'
Probe 1597: 5'-GATAGGGACCGAACTGTCTCACGACGTTCTGAACCCAGCT-3'

The specific behaviors of the aforementioned probes are dependent to a significant extent on the assay format in which they are employed. Conversely, the assay format will dictate certain of the optimal design features of particular probes. The "essence" of the probes of the invention is not to be construed as restricted to the specific string of nucleotides in the named probes. For example, the length of these particular oligonucleotides was optimized for use in the dot blot assay (and certain other anticipated assays) described below. It is well known to those skilled in the art that optimal probe length will be a function of the stringency of the hybridization conditions chosen and hence the length of the instant probes may be altered in accordance therewith. Also, in considering sets comprised of more than one probe, it is desirable that all probes behave in a compatible manner in any particular format in which they are employed. Thus, the exact length of a particular probe will to a certain extent, reflect its specific intended use. Again, given the probes of the instant invention, these are familiar considerations to one of ordinary skill in the art.

The "essence" of the probes described herein resides in the discovery and utilization of the specific sequences described above and given in Table 1 and Table 2.

Hybridization Analysis of Probe Behavior:

The sequence comparisons which led to the discovery of the disclosed target sequences suggested that many of the probes should hybridize to a significant number of eubacteria. For the 16S rRNA analyses, some 350 sequences were considered in designing the probes; for the 23S rRNA analyses only about 30 eubacterial sequences were available. Since it is impossible to test every eubacterial strain, greater sequence variation might exist in other eubacterial strains not inspected by sequence analysis which might reduce or eliminate hybridization by the prospective probes to such untested eubacteria. As can be seen in Tables 3, 4 and 5, some probes of extremely broad inclusivity nevertheless fail to hybridize to certain bacteria. Therefore, carefully documenting the hybridization behavior to a large and representative number of eubacteria is an important element in documenting that such probes are capable of detecting all eubacteria or, failing that, for documenting which eubacteria are not detected. Such "failures" may not be clinically significant or alternatively, may be compensated for by appropriate inclusion of other probes of the instant inventions.

Equally as important as the inclusivity behavior of the probes, is their exclusivity behavior, i.e., their reactivity toward non-eubacteria. As mentioned, demonstrating a lack of hybridization to human and fungal rRNAs is of paramount importance in the types of clinical applications envisioned for such probes. Therefore, the behavior of the probes toward representative eubacterial, human and fungal rRNAs was determined by hybridization analysis using a dot blot procedure.

EXAMPLE 1

Dot-blot Analysis of Probe Hybridization Behavior

Dot-blot analysis, in accordance with well known procedures, involves immobilizing a nucleic acid or a population of nucleic acids on a filter such as nitrocellulose, nylon, or other derivatized membranes which readily can be obtained commercially, specifically for this purpose. Either DNA or RNA can be easily immobilized on such a filter and subsequently can be probed or tested for hybridization under any of a variety of conditions (i.e., stringencies) with nucleotide sequences or probes of interest. Under stringent conditions, probes whose nucleotide sequences have greater complementarity to the target sequence will exhibit a higher level of hybridization than probes containing less complementarity. For most of the oligonucleotide probes described herein, hybridization to rRNA targets at 60° C. for 14-16 hours (in a hybridization solution containing 0.9M NaCl, 0.12M Tris-HCl, pH 7.8, 6 mM EDTA, 0.1M KPO4, 0.1% SDS, 0.1% pyrophosphate, 0.002% ficoll, 0.02% BSA, and 0.002% polyvinylpyrrolidine), followed by standard post-hybridization washes to remove unbound and non-specifically hybridized probe (at 60° C. in 0.03M NaCl, 0.004M Tris-HCl, pH 7.8, 0.2 mM EDTA, and 0.1% SDS), would be sufficiently stringent to produce the levels of specificity demonstrated in Tables 3, 4 and 5. The exceptions to these conditions are probe 1738 (which was hybridized at 37° C.), and probe 1746 (which was hybridized at 37° C. and washed at 50° C.).

Techniques also are available in which DNA or RNA present in crude (unpurified) cell lysates can be immobilized without first having to purify the nucleic acid in question (e.g. Maniatis, T., Fritsch, E. F. and Sambrook, J., 1982, Molecular Cloning: A Laboratory Manual).

The dot-blot hybridization data shown in Tables 3, 4 and 5 were generated by hybridization of the indicated probes to purified RNA preparations from the indicated eubacterial, fungal and human specimens. Bacterial and fungal RNAs were purified from pure cultures of the indicated organisms. Mouse RNA was purified from L cells (a tissue culture cell line). Wheat germ RNA was purified from a commercial preparation of that cereal product. Human blood and stool RNAs were purified from appropriate specimens obtained from normal, healthy individuals.

Purified RNA was used, rather than cell lysates for a number of simple technical reasons. The most important of these relate to proper interpretation of the relative signal arising from the hybridization of any particular probe to individual organisms. RNA content per cell is known to vary widely among different bacteria and varies even more between bacteria and eukaryotic cells. In addition, the specific metabolic status of cells at the time of harvest can have a profound influence on the amount and integrity of the RNA recovered. Some bacteria, for example, begin to degrade their RNA very rapidly upon reaching the stationary growth phase. The organisms represented in Tables 3, 4 and 5 comprise an extremely diverse collection in every respect. Represented are Gram positive and Gram negative bacteria, photosynthetic and chemosynthetic, heterotrophic and lithotrophic, and anaerobic and aerobic metabolisms. By using known, equivalent amounts of purified RNA in the individual "dots," relative levels of hybridization of each probe to each organism can be meaningfully compared without regard to the idiosyncracies of nucleic acid preparation from individual types of bacteria represented.

RNA was prepared by a variation on standard published methods which has been developed in our laboratory (W. Weisburg, unpublished). The method rapidly yields bulk high molecular weight RNA in a highly purified but relatively unfractionated form. Little or no DNA, or low molecular weight RNA species are found in RNA prepared in this fashion.

A large proportion of the RNA is 16S and 23S rRNA (18S and 28S rRNA in eukaryotes) as is true of the RNA in the intact cells. The method is rapid and convenient, but otherwise is not relevant to interpretation of the dot-blot results presented in Tables 3, 4 and 5. Most other currently accepted methods available in the literature which yield RNA of reasonable intactness will yield equivalent hybridization results.

For the hybridization experiments reported in Tables 3, 4 and 5, probes were end-labeled with radioactive 32-phosphorous, using standard procedures. Following hybridization and washing as described above, the hybridization filters were exposed to X-ray film and the intensity of the signal evaluated with respect to that of control RNA spots containing known amount of target RNA of known sequence.

A scale of hybridization intensity ranging from ++++ (hybridization signal equivalent to that of control spots) to + (barely detectable even after long exposure of the x-ray film) has been used to compare hybridization signals between organisms and probes. +++ signal indicates a very strong signal only slightly less intense than control spots. ++ indicates a clearly discernible hybridization signal, but one that is noticeably weaker than the control spots. Note that while more "quantitative" ways to record hybridization signal are available, they are much more cumbersome to employ and, in our experience, not really any more useful for probe evaluation than the method employed in Tables 3, 4 and 5. In fact, because of certain uncontrollable variables in spotting exactly equivalent amounts of target RNA (of equivalent intactness) from such disparate organisms, numerically more precise counting methods are only deceptively more quantitative. In our experience, an organism generating a ++ or greater signal to a particular probe is easily distinguished from one generating a "−" signal. This is true of a variety of assay formats that have been tested.

Figure 2:
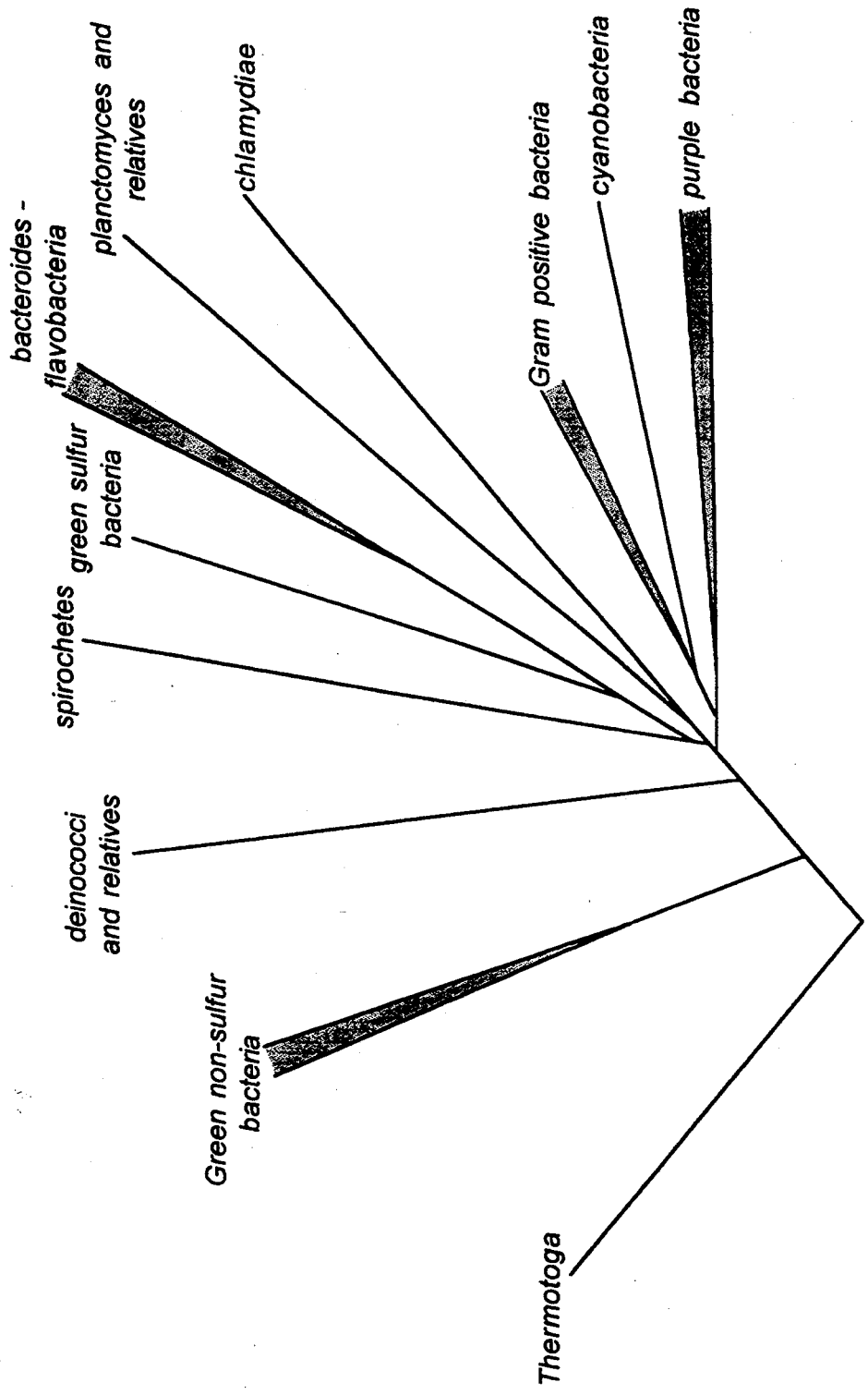
FIG. 2—Shows a more detailed evolutionary tree of the eubacterial kingdom (ibid.). So far about 10 major divisions/phyla have been defined based on 16S rRNA sequence comparisons. Certain discriminations among eubacterial divisions can be important in a clinical context and certain of the probes of the present invention do exhibit preferential hybridization to one or more or the eubacterial divisions. Therefore, the test organisms listed in Tables 3, 4 and 5 are grouped according to the divisions shown in FIG. 2 so that significant patterns of hybridization may be most easily discerned.

As is evident in Tables 3 and 4, 23S rRNA-targeted probes 1600, 1602, 1596, 1526 and 1512 and 16S rRNA-targeted probes, 1738, 1660, 1659, 1739, 1740, 1741 and 1743 hybridize most extensively among the eubacteria and are thus the most preferred. Other probes hybridize in a variety of patterns to subgroups of eubacteria and would be preferred for the detection of those subgroups or as components of more broadly inclusive probe sets. For example, probes 1599, 1656, 1744, 1745 and 1746 hybridize preferentially to Gram positive bacteria. Probes 1657, 1598 and 1595 hybridize preferentially to gram-negative bacteria, particularly to members of the so-called "purple bacterial" division (FIG. 2 and Table 5).

Other probes exhibit other useful patterns of hybridization as is evident upon inspection of the data in Tables 3, 4 and 5. These probes can be combined in a variety of ways to create probe sets which exhibit the combined hybridization properties of the component probes. An example of one such hybridization format is given below (Example 2).

Alternatively, the probes could be used in a variety of subtractive hybridization schemes in which specific rRNA molecules are removed from the pool present in a mixed population of organisms prior to or simultaneous with the target organism-specific probes (e.g. Collins, European Patent Application 87309308.2).

EXAMPLE 2

Dual Probe, Sandwich Hybridization Assay

The probes of the present invention or derivatives thereof can be advantageously employed in a variety of other hybridization formats. One such format is a dual probe, sandwich-type hybridization assay such as that described, for example, in U.S. Ser. Nos. 277,579; 169,646, or 233,683. In such a dual probe application, one probe (for example, probe 1602 or a derivative) would be ideally modified at its 3' terminus to contain a tract of about 20–200 deoxyadenosine (dA) residues. This would be used to "capture" the target rRNA (following liquid hybridization) from the test sample onto a solid support (e.g., beads, plastic surface, filter, etc.) which had been suitably derivatized with poly-deoxythymidine (dT) for this purpose. A second probe (for example, probe 1596 or derivative) would then be advantageously used as the detection probe and would be suitably derivatized with some detectable ligand (e.g. 32-P, fluorescein, biotin, etc.). Detection of the presence of the target nucleic acid in a test sample then would be indicated by capture of the detection ligand onto the solid surface through the series of hybridization interactions:

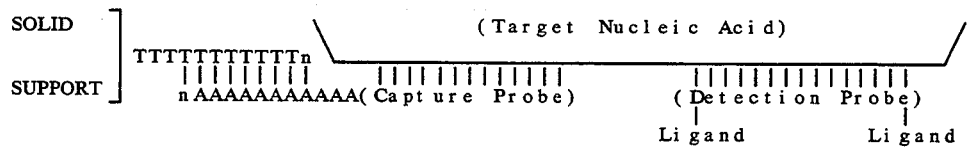

This could occur only if the target nucleic acid is present in the test sample. In principle, the above scheme could be employed with multiple capture and detection probes (probe sets) for the purpose of, for example, improving inclusivity or enhancing sensitivity of the assay.

EXAMPLE 3

PCR Amplification of 16S rRNAs

The polymerase chain reaction (PCR) is a well known method for amplifying target nucleic acid by "copying" the nucleic acid sequences located between two target sequences U.S. Pat. No. 4,683,202). The PCR process could be useful in an assay for the diagnosis of, for example, a non-viral pathogen by amplifying the genes encoding the pathogen's rRNA or rRNA genes and subsequently detecting that product. Implementation of this diagnostic strategy requires the invention of primers capable of amplifying the rRNA of the targeted organism(s). A second important application of such primers is in cloning amplified rRNA genes, and a third application is the direct sequencing of amplified rRNA genes.

Probes 1638, 1642, 1643, 1637, 1639, 1640 and 1641 may be ideally used as primers for enzymatically copying and/or amplifying eubacterial 16S rRNAs or the genes encoding them. Details of the PCR procedure vary slightly depending on whether the target nucleic acid is single or double stranded, and whether it is DNA or RNA. However, the principle is the same in either case. Briefly, the steps are as follows:

1) Double-stranded DNA is denatured,

2) Oligonucleotide primers complimentary to each of the sister DNA strands are annealed, and 3) deoxynucleotide triphosphate precursors are incorporated into newly synthesized sister DNA strands by extension of the primers from their 3' termini using DNA polymerase and/or reverse transcriptase.

Thus, a pair of oligonucleotide primers are required for the PCR reaction, one complementary to each strand within the target gene. They are positioned such that the newly synthesized product of one primer is also a target/template for the other primer. Thus the target nucleotide sequence located between the two primer annealing sites may be amplified many fold by repeating the steps listed above 20 to 30 times.

Probes 1638, 1642, 1643, 1637, 1639, 1640 and 1641 are suitable for use as primers for enzymatically copying and/or amplifying eubacterial 16S rRNAs or the genes encoding them. That is, as a set, they will anneal very broadly among eubacterial rRNAs and rRNA genes and so will amplify any eubacterial rRNA sequences present in a sample.

Probes 1637, 1639, 1640 and 1641 hybridize to the 16S rRNA (or rRNA-like strand of the ribosomal RNA gene) near its 3' end (Table 1). The template strand is read in the 3' to 5' direction producing an rRNA-complementary strand with the primer itself incorporated at its 5' terminus.

Probes 1638, 1642, and 1643 hybridize near the 5' end of the rRNA-complementary strand of the rRNA gene or to such a complement produced as described immediately above.

Individually, the above-described 16S rRNA amplification primers have approximately the following specificities:

5' primers:

Probe 1638: most eubacteria
Probe 1642: enterics and relatives
Probe 1643: Borrelia spirochetes 3' primers:

Probe 1637: most eubacteria
Probe 1639: enterics, Deinococcus, Campylobacter
Probe 1640: most eubacteria
Probe 1641: fusobacteria, some Bacillus species In test samples where the target bacterium is known, specific primers can be used. Where the target organism is not specifically known (for example, any eubacterium) all of the above mentioned primers can be used as a set.

The above described primers have been designed to amplify nearly the entire 16S rRNA sequence. Any of the other probes of the present invention or derivatives thereof can be used to amplify sub-segments of the 16S and 23S rRNAs or genes in a fashion similar to that just described.

Any such primers can be modified in a great number of ways to, for example, incorporate RNA polymerase promoters, cloning sites, etc. into the amplified transcripts.

While the description of the invention has been made with reference to detecting rRNA, it will be readily understood that the probes described herein and probes complementary to those described herein also will be useful for the detection of the genes (DNA) which specify the rRNA and, accordingly, such probes are to be deemed equivalents to the described probes and encompassed within the spirit and scope to the present invention and the appended claims.

TABLE 1

16S rRNA-TARGETED PROBES AND TARGET SEQUENCES

```
                    8                                    38
                    |                                    |
CONS-90%
E. coli             AGAGUUUGAUC  UGGCUCAG     GAACGCUGGCG
                    AGAGUUUGAUCAUGGCUCAGAUUGAACGCUGGCG
Probe 1738     5'-AAAUUGAGAGUUUGAUCAUGGCUCAGAUUGAACGCUGGCG
Probe 1744                  3'-TCTCAAACTAGGACCGAGTC-5'
Probe 1638                  3'-TCAAACTAGGACCGAGTCCTGCTTGCGAC-5'
Probe 1642                  5'-AGAGTTTGATCCTGGCTCAG-3'
Probe 1643                  5'-AGAGTTTGATCATGGCTCAG-3'
                            5'-AGAGTTTGATCCTGGCTTAG-3'

313                               357
                      |                                  |
CONS-90%     G CACA UGG ACUGAGACACGG  CCA ACUCCUACGGGAGGCAGCAGU
E. coli      GCCACAACUGGAACUGAGACACGGUCCAGACUCCUACGGGAGGCAGCAGUGG
Probe 1660              3'-TGTGACCTTGACTCTGTGCCAGGTCGAGGATGCCCTCCGTCGTC-5'
Probe 1659                       3'-TGAGGATGCCCTCCGTCGTC-5'

504                               535
                      |                                  |
CONS-90%     C  CGGCUAACU  GUGCCAGCAGCCGCGGUAAUAC
E. coli      CACCGGCUAACUACCCCGCUGCCAGCAGCCGCGGUAAUACGG
Probe 1661            3'-GCCGATTGAGGGCACGGTCGTCGGCGCCATTAT-5'

764                               810
                      |                                  |
CONS-90%     G  CGAAAGCGUGGGGAGC  AACAGGAUUAGAUACCCUGGUAGUCCACGC  U
E. coli      GUGCGAAAGCGUGGGGAGCAAACAGGAUUAGAUACCCUGGUAGUCCACGCCGU
Probe 1739           3'-GCTTTCGCACCCCTCGTTTGTCCTAATCTATGGGCCATCAGGTGCG-5'

1044                              1114
                      |                                   |
CONS-90%     ACAGGUG  UGCAUGG  UGUCGUCAGCUCGUG  CGUGAG  UGUUGGGUUAAGUCCCGCAACGAGCGCAACCC
E. coli      GAGACAGGUGCUGCAUGGCUGUCGUCAGCUCGUGUCGUGUGAAAUGUGGGUUAAGUCCCGCAACGAGCGCAACCCUA
Probe 1745         3'-TGTCCACCACGTTACCAACGACCAGTCGA-5'
Probe 1740                         3'-TACGTACCGACAGCAGTCGAGCAGCAGTCGAGCAGCAGTCGAGCACTCTACAGCCCAATTCAGGGCGTTGCTCGCGTTGGG-5'
Probe 1741                         3'-TACGTACCGACAGCAGTCGAGCAGCAGTCGAGCAGCACTC-5'
Probe 1742                                           3'-TACAGCCCAATTCAGGGCGTTGCTCGCGTTGGG-5'

1188                              1216
                      |                                   |
CONS-90%     GGA  GACGUCAA  UC  UCAUG  CCCUUA  G
E. coli      GGGAUGACGUCAAGUCAUCAUGGCCCUUACGACCA
Probe 1746            3'-TACTGCAGTTTAGTACGGGGAATACT-5'

1369                              1395
                      |                                   |
CONS-90%     CGGUGAAUACGUUC  CGGG  CUUGUACACA
E. coli      CCACGGUGAAUACGUUCCCGGGCCUUGUACACA
Probe 1743              3'-GCCACTTATGCAAGGGCCCGGAACATG-5'

1492                              1541
                      |                                   |
CONS-90%     AAGUCGUAACAAGGUA  CC UA   GAA  UG GG UGGAU ACCUCCUUU
E. coli      GUGAAGUCGUAACAAGGUAACCGUAGGGGAACCUGCGGUUGGAUCACCUCCUUA-3'
```

| | |
|---|---|
| E. coli# | |
| CONS-90% | |
| E. coli | |
| Probe 1738 | |
| Probe 1744 | |
| Probe 1638 | |
| Probe 1642 | |
| Probe 1643 | |

TABLE 1-continued 16S rRNA-TARGETED PROBES AND TARGET SEQUENCES

| | | |
|---|---|---|
| Probe 1637 | | 3'-CCGACCTAGTGGAGGAA-5' |
| Probe 1639 | 3'-TTCAGCATTGTTCCATTGGCA-5' | |
| Probe 1640 | 3'-TTCAGCATTGTTCCATCGGCA-5' | |
| Probe 1641 | 3'-TTCAGCATTGTTCCATAGGCA-5' | |

TABLE 2

23S rRNA-TARGETED PROBES AND TARGET SEQUENCES

```
E. coli #s    442                                              481
              |                                                |
CONS-90%      GACCGAUAG  G  AC  AGUACCGUGAGGGAAAGG  GAAAAG  AC
E. coli 23S   ACUGACCGAUAGUGAACCAGUACCGUGAGGGAAAGGCGAAAAGAAC
Probe 1730    3'-CTGGCTATCRCTTGGTCATGGCRCTCCCTTTCCRCTTTTC-5'
Probe 1731    3'-CTGGCTATCGCTTGGTCATGGCGCTCCCTTTCCGCTTTTC-5'

E. coli #s    1049                                             1088
              |                                                |
CONS-90%      A ACA  C  AGGA  GUUGGCUUAGAAGCAGCCA  C  UU  AAAGA    G
E. coli 23S   AGACAGCCAGGAUGUUGGCUUAGAAGCAGCCAUCAUUUAAAGAAAG
Probe 1658    3'-GTTGGTCCTACAACCGAATCTTCGTCGGTGGGAAATTTCT-5'

E. coli #s    1597                                                 1639
              |                                                    |
CONS-90%         CGUACC   AAACCGACACAGGU  G     G    A    C    AG
E. coli 23S   UCAAAUCGUACCCCAAACCGACACAGGUGGUCAGGUAGAGAAUACCAAG
Probe 1656    3'-CGGGCATGGCGTTTGGCTGTGTCCATC-5'
Probe 1657       3'-GCATGGGGTTTGGCTGTGTCCACCAGTCCATCTCTTATGG-5'

E. coli #s    1664                                             1703
              |                                                |
CONS-90%         AAGGAACU  GCAAA  U    CCGUAACUUCGG  A  AAGG
E. coli 23S   GUGAAGGAACUAGGCAAAAUGGUGCCGUAACUUCGGGAGAAGGCAC
Probe 1653    3'-TTCCTTGATCCGTTTTACGGGGGCATTGAAGCCCTCTTCC-5'
Probe 1654    3'-TTCCTTGAGCCGTTTTACTGGGGCATTGAAGCCCTCTTCC-5'
Probe 1655    3'-TTCCTTGAGCCGTTTTACCACGGCATTGAAGCCCTCTTCC-5'

E. coli #s    1831                              1860
              |                                 |
CONS-90%      GAC  CCUGCCC  GUGC  GGAAGGUUAA   G
E. coli 23S   GACGCCUGCCCGGUGCCGGAAGGUUAAUUGAUGGGG
Probe 1651    3'-CGGACGGGCCACGACCTTCCAATTCTCCTC-5'

E. coli #s    1851                                             1890
              |                                                |
CONS-90%      AGGUUAA    G    U    G  AAG    A    GAAGCC
E. coli 23S   AGGUUAAUUGAUGGGGUUAGCGCAAGCGAAGCUCUUGAUCGAAGCC
Probe 1652    3'-AATTAACTACCCCAGTCGCGTTCGCTTCGGGGACTAGCTT-5'

E. coli #s    1889                                             1928
              |                                                |
CONS-90%      GAAGCCCC  GU  AACGGCGGCCGUAACUAUAACGGUCCUAAGGU
E. coli 23S   UCGAAGCCCCGGUAAACGGCGGCCGUAACUAUAACGGUCCUAAGGU
Probe 1512    3'-TTCGGGGTCATTTGCCGCCGGCATTGATATTGCCAGGATT-5'

E. coli #s    1925                                                 1968
              |                                                    |
CONS-90%      GUCCUAAGGUAGCGAAAUUCCUUGUCGGGUAAGUUCCGACC  GCACGAA
E. coli 23S   GUCCUAAGGUAGCGAAAUUCCUUGUCGGGUAAGUUCCGACCUGCACGAAU
Probe 1256    3'-GATTCCATCGCTTTAAGGAACAGCCCATTCAAGGCTGG-5'
Probe 1511       3'-CCATCGCTTTAAGGAACAGCCCATTCAAGGCTGGGCGTGC-5'
Probe 1398    3'-GATTCCATCGCTTTAAGGAACAGCCAATTTATGGCTGG-5'

E. coli #s    2442                                             2481
              |                                                |
CONS-90%      AC  C  GGGGAUAACAGGCU  AU   C    CC  AG  GU  CA  AUCG  CG
E. coli 23S   ACUCCGGGGAUAACAGGCUGAUACCGCCCAAGAGUUCAUAUCGACG
Probe 1595    3'-GGCCCCTATTGTCCGACTATGGCGGGTTCTCAAGTATAGC-5'

E. coli #s    2490                                             2529
              |                                                |
CONS-90%         GUUUGGCACCUCGAUGUCGGCUC  UC  CAUCCUGGGGCUG  AG
E. coli 23S   GGUGUUUGGCACCUCGAUGUCGGCUCAUCACAUCCUGGGGCUGAAG
Probe 1600    3'-CAAACCGTGGAGCTACAGCCGAGTAGAGTAGGACCCCGAC-5'
Probe 1601    3'-CAAACCGTGGAGCTACAGCCGAGTAGTGTAGGACCCCGAC-5'
Probe 1602    3'-CAAACCGTGGAGCTACAGCCGAGTAGCGTAGGACCCCGAC-5'

E. coli #s    2535                                             2574
              |                                                |
CONS-90%      G   GGUCCCAAGGGU   GGCUGUUCGCC   UUAAAG  GG  ACG  GA
E. coli 23S   GUAGGUCCCAAGGGUAUGGCUGUUCGCCAUUUAAAGUGGUACGCGA
Probe 1598    3'-CCAGGGTTCCCATACCGACAAGCGGTAAATTTCGCCATGC-5'
Probe 1599    3'-CCAGGGTTCCCAACCCGACAAGCGGGTAATTTCGCCGTGC-5'

E. coli #s    2577                                             2616
              |                                                |
CONS-90%      G  GAGCUGGGUU  A  AACGUCGUGAGACAGUU  GGUC  CUAUC
E. coli 23S   GCGAGCUGGGUUUAGAACGUCGUGAGACAGUUCGGUCCCUAUCUGC
Probe 1596    3'-TCGACCCAAGTTTTGCAGCACTCTGTCAAGCCAGGGATAG-5'
Probe 1597    3'-TCGACCCAAGTCTTGCAGCACTCTGTCAAGCCAGGGATAG-5'
```

TABLE 3

DOT BLOT HYBRIDIZATION of 16S rRNA-TARGETED PROBES

| Genus species | strain | div | PROBE HYBRIDIZATION | | | | |
|---|---|---|---|---|---|---|---|
| | | | 1738 | 1739 | 1659 | 1660 | 1661 |
| *Acinetobacter calcoaceticus* | GT0002 | Purple | ++++ | ++++ | ++++ | ++++ | ++++ |
| *Aeromonas sobria* | GT0007 | gamma | ++++ | ++++ | ++++ | ++++ | ++++ |
| *Alteromonas putrefaciens* | GT1945 | " | ++++ | ++++ | ++++ | ++++ | ++++ |
| *Citrobacter amalonaticus* | GT0690 | " | ++++ | ++++ | ++++ | ++++ | ++++ |
| *Citrobacter diversus* | GT0030 | " | ++++ | ++++ | ++++ | ++++ | ++++ |
| *Citrobacter freundii* | GT0687 | " | ++++ | ++++ | ++++ | ++++ | ++++ |
| *Edwardsiella tarda* | GT0569 | " | ++++ | ++++ | ++++ | ++++ | ++++ |
| *Enterobacter agglomerans* | GT0683 | " | ++++ | ++++ | ++++ | ++++ | ++++ |
| *Enterobacter cloacae* | GT0686 | " | ++++ | ++++ | ++++ | ++++ | ++++ |
| *Enterobacter sakazakii* | GT0062 | " | ++++ | ++++ | ++++ | ++++ | ++++ |
| *Escherichia coli* | GT1665 | " | ++++ | ++++ | ++++ | ++++ | ++++ |
| *Escherichia coli* | GT1592 | " | ++++ | ++++ | ++++ | ++++ | ++++ |
| *Escherichia coli* | GT1659 | " | +++ | ++++ | ++++ | ++++ | ++++ |
| *Haemophilus influenza* | GT0244 | " | ++++ | ++++ | ++++ | ++++ | ++++ |
| *Haemophilus ducreyi* | GT0243 | " | ++++ | ++++ | ++++ | ++++ | ++++ |
| *Hafnia alvei* | GT0241 | " | ++++ | ++++ | ++++ | ++++ | ++++ |
| *Morgenella morganii* | GT0303 | " | ++++ | ++++ | ++++ | ++++ | ++++ |
| *Klebsiella pneumoniae* | GT1500 | " | ++++ | ++++ | ++++ | ++++ | ++++ |
| *Proteus mirabilis* | GT1496 | " | ++++ | ++++ | ++++ | ++++ | ++++ |
| *Providencia alcalifaciens* | GT0371 | " | ++++ | ++++ | ++++ | ++++ | ++++ |
| *Pseudomonas aeruginosa* | GT1909 | " | ++++ | ++++ | ++++ | ++++ | ++++ |
| *Salmonella arizona* | GT0799 | " | ++++ | ++++ | ++++ | ++++ | ++++ |
| *Salmonella typhimurium* | GT0389 | " | ++++ | ++++ | ++++ | ++++ | ++++ |
| *Serratia marcescens* | GT0392 | " | ++++ | ++++ | ++++ | ++++ | ++++ |
| *Shigella flexneri* | GT0798 | " | ++++ | ++++ | ++++ | ++++ | ++++ |
| *Vibrio parahaemolyticus* | GT0568 | " | ++++ | ++++ | ++++ | ++++ | ++++ |
| *Xanthomonas maltophilia* | GT0417 | " | ++++ | ++++ | ++++ | ++++ | ++++ |
| *Yersinia enterocolitica* | GT0419 | " | ++++ | ++++ | ++++ | ++++ | ++++ |
| *Alcaligenes faecalis* | GT0610 | Purple | ++++ | ++++ | ++++ | ++++ | ++++ |
| *Branhamella catarrhalis* | GT0014 | beta | +++ | ++++ | ++++ | ++++ | ++++ |
| *Chromobacterium violaceum* | GT2022 | " | ++++ | ++++ | ++++ | ++++ | ++++ |
| *Kingella indologenes* | 0246 | " | ++++ | ++++ | ++++ | ++++ | ++++ |
| *Moraxella osloensis* | GT0301 | " | ++++ | ++++ | ++++ | ++++ | ++++ |
| *Moraxella phenylpyruvica* | GT0302 | " | +++ | ++++ | ++++ | ++++ | ++++ |
| *Borrelia burgdorferi* | | Spiro | ++++ | ++++ | ++++ | ++++ | ++++ |
| *Borrelia turicatae* | | " | ++++ | ++++ | ++++ | ++++ | ++++ |
| *Leptospira interrogans-pomona* | | " | ++++ | +++ | ++++ | ++++ | ++++ |
| *Leptospira biflexa* (Patoc-Patoc) | | " | ++++ | ++ | ++++ | ++++ | ++++ |
| *Leptospira biflexa* (CDC) | | " | ++++ | +++ | ++++ | ++++ | ++++ |
| *Spirochaeta aurantia* | | " | ++++ | ++++ | ++++ | ++++ | ++++ |
| *Bacteroides fragilis* | 25285 | Bact | ++++ | +++ | ++++ | ++++ | ++++ |
| *Bacteroides fragilis* | 29771 | " | ++++ | +++ | ++++ | ++++ | ++++ |
| *Bacteroides thetaiotaomicron* | 0572 | " | ++++ | ++ | ++++ | ++++ | ++++ |
| *Bacteroides melaninogenicus* | 0011 | " | ++++ | ++ | ++++ | ++++ | ++++ |
| *Flavobacterium meningosepticum* | 0237 | " | ++++ | ++++ | ++++ | ++++ | ++++ |
| *Chlamydia psittaci* | | Chlam | − | ++++ | − | +++ | ++++ |
| *Chlamydia trachomatis* | | " | − | ++++ | − | +++ | ++++ |
| *Chlorobium limicola* | | Misc | ++++ | ++++ | ++++ | ++++ | ++++ |
| *Chloroflexus aurantiacus* | Y400 | " | ++++ | ++++ | ++++ | ++++ | ++++ |
| *Deinococcus radiodurans* | 2608 | " | ++++ | ++++ | ++++ | ++++ | ++++ |
| *Planctomyces maris* | 2577 | " | ++++ | ++++ | − | ++++ | ++++ |
| Normal Stool RNA | | | ++++ | ++++ | ++++ | ++++ | ++++ |
| Mouse L-Cell | | | − | + | − | − | ++ |
| Wheat Germ | | | − | − | − | − | ++ |
| Normal Human Blood | | | − | − | − | − | ++ |
| *Candida lusitaniae* | 403-87 | | − | − | − | − | ++++ |
| *Candida parapsilosis* | 882-88 | | − | − | − | − | ++++ |
| *Candida tropicalis* | 224-87 | | − | − | − | − | ++++ |
| *Candida albicans* | 1008-88 | | − | − | − | − | +++ |
| *Candida albicans* | 223-87 | | − | − | − | − | ++++ |
| *Candida albicans* | 819-88 | | − | − | − | − | ++++ |
| *Mycoplasma pneumoniae* | ATCC15531 | " | ++++ | ++++ | ++++ | ++++ | − |
| *Mycoplasma putrefaciens* | ATCC15718 | " | ++++ | ++++ | ++++ | ++++ | ++++ |
| *Peptostreptococcus productus* | ATCC27340 | " | ++++ | ++++ | ++++ | ++++ | ++++ |
| *Planococcus citreus* | ATCC14404 | " | ++++ | ++++ | ++++ | ++++ | ++++ |
| *Staphlyococcus aureus* | GT0399 | " | ++++ | ++++ | ++++ | ++++ | ++++ |
| *Staphylococcus aureus* | GT1711 | " | ++++ | ++++ | ++++ | ++++ | ++++ |
| *Staphylococcus epidermidis* | GT0401 | " | ++++ | ++++ | ++++ | ++++ | ++++ |
| *Staphylococcus haemolyticus* | ATCC29970 | " | ++++ | ++++ | ++++ | ++++ | ++++ |
| *Streptococcus agalactiae* | GT0405 | " | ++++ | ++++ | ++++ | ++++ | ++++ |
| *Streptococcus bovis* | GT0668 | " | ++++ | ++++ | ++++ | ++++ | ++++ |
| *Streptococcus faecalis* | GT0406 | " | ++++ | ++++ | ++++ | ++++ | ++++ |
| *Streptococcus morbillorum* | GT2194 | " | ++ | ++++ | ++++ | ++++ | ++++ |
| *Streptococcus mutans* | GT0412 | " | +++ | ++++ | ++++ | ++++ | ++++ |
| *Streptococcus pneumoniae* | GT0408 | " | +++ | ++++ | ++++ | ++++ | ++++ |
| *Streptococcus salivarius* | GT0410 | " | ++++ | ++++ | ++++ | ++++ | ++++ |
| *Streptococcus sanguis* | GT0411 | " | ++++ | ++++ | ++++ | ++++ | ++++ |
| *Bifidobacterium dentium* | GT0012 | hiG+C | − | ++++ | ++++ | ++++ | ++++ |

TABLE 3-continued

DOT BLOT HYBRIDIZATION of 16S rRNA-TARGETED PROBES

| | | | | | | | |
|---|---|---|---|---|---|---|---|
| Corynebacterium genitalium | GT0045 | Gm + | ++++ | ++++ | ++++ | ++++ | ++++ |
| Corynebacterium glutamicum | GT2120 | " | ++++ | ++++ | ++++ | ++++ | ++++ |
| Corynebacter. pseudodiphtheriticum | GT2119 | " | ++++ | ++++ | ++++ | ++++ | ++++ |
| Corynebacterium pseudotuberculosis | GT2122 | " | ++++ | ++++ | ++++ | ++++ | ++++ |
| Corynebacterium pyogenes | GT2121 | " | ++++ | ++++ | ++++ | ++++ | ++++ |
| Corynebacterium xerosis | GT0046 | " | ++ | +++ | ++++ | ++++ | ++++ |
| Mycobacterium bovis | BCG | " | ++ | ++++ | ++++ | ++++ | ++++ |
| Mycobacterium kansasii | | " | ++++ | ++++ | ++++ | ++++ | ++++ |
| Nocardia asteroides | GT2191 | " | ++++ | ++++ | ++++ | ++++ | ++++ |
| Rhodococcus rhodochrous | | Misc | ++++ | ++++ | ++++ | ++++ | ++++ |
| Aerococcus viridans | GT2116 | Gm + | ++++ | ++++ | ++++ | ++++ | ++++ |
| Fusobacterium necrophorum | GT0238 | " | ++++ | ++++ | ++++ | ++++ | ++++ |
| Fusobacterium prausnitzii | ATCC27768 | " | ++++ | ++++ | ++++ | ++++ | ++++ |
| Gemella haemolysans | GT2118 | " | ++++ | ++++ | ++++ | ++++ | ++++ |
| Heliobacillus mobilis | | " | ++++ | ++++ | ++++ | ++++ | ++++ |
| Phormidium ectocarpi | | Cyano | ++++ | ++ | ++++ | ++++ | ++++ |
| Plectonema boryanum | | " | ++++ | ++ | ++++ | ++++ | ++++ |
| Neisseria gonorrhoeae | GT0315 | " | ++++ | ++++ | ++++ | ++++ | ++++ |
| Neisseria meningitidis | GT0349 | " | ++++ | ++++ | ++++ | ++++ | ++++ |
| Pseudomonas acidovorans | GT0376 | " | ++++ | ++++ | ++++ | ++++ | ++++ |
| Pseudomonas cepacia | GT2015 | " | ++++ | ++++ | ++++ | ++++ | ++++ |
| Rhodocyclus gelatinosa | ATCC17013 | " | ++++ | ++++ | ++++ | ++++ | ++++ |
| Vitreoscilla stercoraria | | " | ++++ | ++++ | ++++ | ++++ | ++++ |
| Achromobacter xerosis | GT0810 | Purple | ++++ | ++++ | ++++ | ++++ | ++++ |
| Acidiphilium cryptum | ATCC33463 | alpha | ++++ | ++++ | ++++ | ++++ | ++++ |
| Agrobacterium tumefaciens | GT2021 | " | ++++ | ++++ | ++++ | ++++ | ++++ |
| Brucella abortus | ATCC23448 | " | ++++ | ++++ | ++++ | ++++ | ++++ |
| Flavobacterium capsulatum | GT2025 | " | ++++ | ++++ | ++++ | ++++ | ++++ |
| Mycoplana bullata | GT2023 | " | ++++ | ++++ | ++++ | ++++ | ++++ |
| Pseudomonas diminuta | GT2020 | " | ++++ | ++++ | ++++ | ++++ | ++++ |
| Rhodobacter sphaeroides | ATCC17023 | " | ++++ | ++++ | ++++ | ++++ | ++++ |
| Rhodospirillum rubrum | ATCC25903 | " | ++++ | ++++ | ++++ | ++++ | ++++ |
| Thiobacillus versutus | ATCC25364 | " | ++++ | ++++ | ++++ | ++++ | ++++ |
| Desulfovibrio desulfuricans | ATCC 7757 | delta | ++++ | ++++ | ++++ | ++++ | ++++ |
| Cardiobacterium hominis | GT2095 | Gm − | ++++ | ++++ | ++++ | ++++ | ++++ |
| Francisella tularensis | GT2172 | Gm − | ++++ | ++++ | ++++ | ++++ | ++++ |
| Campylobacter jejuni | GT0022 | Campy | ++++ | ++++ | ++++ | ++++ | ++++ |
| Campylobacter pylori | GT0026 | " | ++++ | ++++ | ++++ | ++++ | ++++ |
| Campylobacter sputorum | GT0027 | " | ++++ | ++++ | ++++ | ++++ | ++++ |
| Bacillus brevis | GT0803 | lowG+C | ++++ | ++++ | ++++ | ++++ | ++++ |
| Bacillus subtilis | GT0804 | Gm + | ++++ | ++++ | ++++ | ++++ | ++++ |
| Clostridium clostridioforme | ATCC25537 | " | ++++ | ++++ | ++++ | ++++ | ++++ |
| Clostridium sordellii | GT0567 | " | ++++ | ++++ | ++++ | ++++ | ++++ |
| Clostridium sporogenes | ATCC 3587 | " | ++++ | ++++ | ++++ | ++++ | ++++ |
| Clostridium histolyticum | ATCC19401 | " | ++++ | ++++ | ++++ | ++++ | ++++ |
| Clostridium perfringens | ATCC13124 | " | ++++ | ++++ | ++++ | ++++ | ++++ |
| Clostridium ramosum | ATCC25582 | " | ++++ | ++++ | ++++ | ++++ | ++++ |
| Kurthia zopfii | ATCC33403 | " | ++++ | ++++ | ++++ | ++++ | ++++ |
| Lactobacillus acidophilus | GT0256 | " | ++++ | ++++ | ++++ | ++++ | ++++ |
| Lactobacillus plantarum | GT0258 | " | ++++ | ++++ | ++++ | ++++ | ++++ |
| Listeria monocytogenes | IG3299 | " | ++++ | ++++ | ++++ | ++++ | ++++ |

| | | | PROBE HYBRIDIZATION | | | |
|---|---|---|---|---|---|---|
| Genus species | strain | div | 1740 | 1741 | 1742 | 1743 |
| Acinetobacter calcoaceticus | GT0002 | Purple | ++++ | ++++ | ++++ | ++++ |
| Aeromonas sobria | GT0007 | gamma | ++++ | ++++ | ++++ | ++++ |
| Alteromonas putrefaciens | GT1945 | " | ++++ | ++++ | ++++ | ++++ |
| Citrobacter amalonaticus | GT0690 | " | ++++ | ++++ | ++++ | ++++ |
| Citrobacter diversus | GT0030 | " | ++++ | ++++ | ++++ | ++++ |
| Citrobacter freundii | GT0687 | " | ++++ | ++++ | ++++ | ++++ |
| Edwardsiella tarda | GT0569 | " | ++++ | ++++ | ++++ | ++++ |
| Enterobacter agglomerans | GT0683 | " | ++++ | ++++ | ++++ | ++++ |
| Enterobacter cloacae | GT0686 | " | ++++ | ++++ | ++++ | ++++ |
| Enterobacter sakazakii | GT0062 | " | ++++ | ++++ | ++++ | ++++ |
| Escherichia coli | GT1665 | " | ++++ | ++++ | ++++ | ++++ |
| Escherichia coli | GT1592 | " | ++++ | ++++ | ++++ | ++++ |
| Escherichia coli | GT1659 | " | ++++ | ++++ | ++++ | ++++ |
| Haemophilus influenza | GT0244 | " | ++++ | ++++ | ++++ | ++++ |
| Haemophilus ducreyi | GT0243 | " | ++++ | ++++ | ++++ | ++++ |
| Hafnia alvei | GT0241 | " | ++++ | ++++ | ++++ | ++++ |
| Morgenella morganii | GT0303 | " | ++++ | ++++ | ++++ | ++++ |
| Klebsiella pneumoniae | GT1500 | " | ++++ | ++++ | ++++ | ++++ |
| Proteus mirabilis | GT1496 | " | ++++ | ++++ | ++++ | ++++ |
| Providencia alcalifaciens | GT0371 | " | ++++ | ++++ | ++++ | ++++ |
| Pseudomonas aeruginosa | GT1909 | " | ++++ | ++++ | ++++ | ++++ |
| Salmonella arizona | GT0799 | " | ++++ | ++++ | ++++ | ++++ |
| Salmonella typhimurium | GT0389 | " | ++++ | ++++ | ++++ | ++++ |
| Serratia marcescens | GT0392 | " | ++++ | ++++ | ++++ | ++++ |
| Shigella flexneri | GT0798 | " | ++++ | ++++ | ++++ | ++++ |
| Vibrio parahaemolyticus | GT0568 | " | ++++ | ++++ | ++++ | ++++ |
| Xanthomonas maltophilia | GT0417 | " | ++++ | ++++ | ++++ | ++++ |

TABLE 3-continued
DOT BLOT HYBRIDIZATION of 16S rRNA-TARGETED PROBES

| Organism | Strain | Group | | | | |
|---|---|---|---|---|---|---|
| Yersinia enterocolitica | GT0419 | " | ++++ | ++++ | ++++ | ++++ |
| Alcaligenes faecalis | GT0610 | Purple | ++++ | ++++ | ++++ | ++++ |
| Branhamella catarrhalis | GT0014 | beta | ++++ | ++++ | ++++ | ++++ |
| Chromobacterium violaceum | GT2022 | " | ++++ | ++++ | ++++ | ++++ |
| Kingella indologenes | 0246 | " | ++++ | ++++ | ++++ | ++++ |
| Moraxella osloensis | GT0301 | " | ++++ | ++++ | ++++ | ++++ |
| Moraxella phenylpyruvica | GT0302 | " | ++++ | ++++ | ++++ | ++++ |
| Borrelia burgdorferi | | Spiro | ++++ | ++++ | ++++ | ++++ |
| Borrelia turicatae | | " | ++++ | ++++ | ++++ | ++++ |
| Leptospira interrogans-pomona | | " | ++++ | ++++ | ++++ | ++ |
| Leptospira biflexa (Patoc-Patoc) | | " | ++++ | ++++ | ++++ | + |
| Leptospira biflexa (CDC) | | " | ++++ | ++++ | ++++ | ++ |
| Spirochaeta aurantia | | " | ++++ | ++++ | ++++ | ++++ |
| Bacteroides fragilis | 25285 | Bact | ++++ | ++++ | − | ++++ |
| Bacteroides fragilis | 29771 | " | ++++ | ++++ | − | ++++ |
| Bacteroides thetaiotaomicron | 0572 | " | ++++ | ++++ | − | ++++ |
| Bacteroides melaninogenicus | 0011 | " | ++++ | ++++ | − | ++++ |
| Flavobacterium meningosepticum | 0237 | " | ++++ | ++++ | ++++ | ++++ |
| Chlamydia psittaci | | Chlam | ++++ | ++++ | ++++ | ++++ |
| Chlamydia trachomatis | | " | ++++ | ++++ | ++++ | ++++ |
| Chlorobium limicola | | Misc | ++++ | ++++ | ++++ | + |
| Chloroflexus aurantiacus | Y400 | " | ++++ | ++++ | ++++ | ++++ |
| Deinococcus radiodurans | 2608 | " | ++++ | ++++ | ++++ | ++++ |
| Planctomyces maris | 2577 | " | ++++ | ++++ | − | − |
| Normal Stool RNA | | | ++++ | ++++ | ++++ | ++++ |
| Mouse L-Cell | | | − | − | − | − |
| Wheat Germ | | | − | − | − | − |
| Normal Human Blood | | | − | − | − | − |
| Candida lusitaniae | 403-87 | | − | − | − | − |
| Candida parapsilosis | 882-88 | | − | − | − | − |
| Candida tropicalis | 224-87 | | − | − | − | − |
| Candida albicans | 1008-88 | | − | − | − | − |
| Candida albicans | 223-87 | | − | − | − | − |
| Candida albicans | 819-88 | | − | − | − | − |
| Mycoplasma pneumoniae | ATCC15531 | " | ++++ | ++++ | ++++ | − |
| Mycoplasma putrefaciens | ATCC15718 | " | ++++ | ++++ | ++++ | − |
| Peptostreptococcus productus | ATCC27340 | " | ++++ | ++++ | ++++ | ++++ |
| Planococcus citreus | ATCC14404 | " | ++++ | ++++ | ++++ | ++++ |
| Staphlyococcus aureus | GT0399 | " | ++++ | ++++ | ++++ | ++++ |
| Staphylococcus aureus | GT1711 | " | ++++ | ++++ | ++++ | ++++ |
| Staphylococcus epidermidis | GT0401 | " | ++++ | ++++ | ++++ | ++++ |
| Staphylococcus haemolyticus | ATCC29970 | " | ++++ | ++++ | ++++ | ++++ |
| Streptococcus agalactiae | GT0405 | " | ++++ | ++++ | ++++ | ++++ |
| Streptococcus bovis | GT0668 | " | ++++ | ++++ | ++++ | ++++ |
| Streptococcus faecalis | GT0406 | " | ++++ | ++++ | ++++ | ++++ |
| Streptococcus morbillorum | GT2194 | " | ++++ | ++++ | ++++ | ++++ |
| Streptococcus mutans | GT0412 | " | ++++ | ++++ | ++++ | ++++ |
| Streptococcus pneumoniae | GT0408 | " | ++++ | ++++ | ++++ | ++++ |
| Streptococcus salivarius | GT0410 | " | ++++ | ++++ | ++++ | ++++ |
| Streptococcus sanguis | GT0411 | " | ++++ | ++++ | ++++ | ND |
| Bifidobacterium dentium | GT0012 | hiG+C | ++++ | ++++ | ++++ | ++++ |
| Corynebacterium genitalium | GT0045 | Gm + | ++++ | ++++ | ++++ | ++++ |
| Corynebacterium glutamicum | GT2120 | " | ++++ | ++++ | ++++ | ++++ |
| Corynebacter. pseudodiphtheriticum | GT2119 | " | ++++ | ++++ | ++++ | ++++ |
| Corynebacterium pseudotuberculosis | GT2122 | " | ++++ | ++++ | ++++ | ++++ |
| Corynebacterium pyogenes | GT2121 | " | ++++ | ++++ | ++++ | ++++ |
| Corynebacterium xerosis | GT0046 | " | ++++ | ++++ | ++++ | ++++ |
| Mycobacterium bovis | BCG | " | ++++ | ++++ | ++++ | ++++ |
| Mycobacterium kansasii | | " | ++++ | ++++ | ++++ | ++++ |
| Nocardia asteroides | GT2191 | " | ++++ | ++++ | ++++ | ++++ |
| Rhodococcus rhodochrous | | Misc | ++++ | ++++ | ++++ | ++++ |
| Aerococcus viridans | GT2116 | Gm + | ++++ | ++++ | ++++ | − |
| Fusobacterium necrophorum | GT0238 | " | ++++ | ++++ | ++++ | ++++ |
| Fusobacterium prausnitzii | ATCC27768 | " | ++++ | ++++ | ++++ | ++++ |
| Gemella haemolysans | GT2118 | " | ++++ | ++++ | ++++ | ++++ |
| Heliobacillus mobilis | | " | ++++ | ++++ | ++++ | ++++ |
| Phormidium ectocarpi | | Cyano | ++++ | ++++ | ++++ | ++++ |
| Plectonema boryanum | | " | ++++ | ++++ | ++++ | ++++ |
| Neisseria gonorrhoeae | GT0315 | " | ++++ | ++++ | ++++ | ++++ |
| Neisseria meningitidis | GT0349 | " | ++++ | ++++ | ++++ | ++++ |
| Pseudomonas acidovorans | GT0376 | " | ++++ | ++++ | ++++ | ++++ |
| Pseudomonas cepacia | GT2015 | " | ++++ | ++++ | ++++ | ++++ |
| Rhodocyclus gelatinosa | ATCC17013 | " | ++++ | ++++ | ++++ | ++++ |
| Vitreoscilla stercoraria | | " | ++++ | ++++ | ++++ | ++++ |
| Achromobacter xerosis | GT0810 | Purple | ++++ | ++++ | ++++ | ++++ |
| Acidiphilium cryptum | ATCC33463 | alpha | ++++ | ++++ | ++++ | ++++ |
| Agrobacterium tumefaciens | GT2021 | " | ++++ | ++++ | ++++ | ++++ |
| Brucella abortus | ATCC23448 | " | ++++ | ++++ | ++++ | ++++ |
| Flavobacterium capsulatum | GT2025 | " | ++++ | ++++ | ++++ | + |
| Mycoplana bullata | GT2023 | " | ++++ | ++++ | ++++ | ++++ |
| Pseudomonas diminuta | GT2020 | " | ++++ | ++++ | ++++ | ++++ |

TABLE 3-continued
DOT BLOT HYBRIDIZATION of 16S rRNA-TARGETED PROBES

| | | | | | | |
|---|---|---|---|---|---|---|
| Rhodobacter sphaeroides | ATCC17023 | " | ++++ | ++++ | ++++ | ++++ |
| Rhodospirillum rubrum | ATCC25903 | " | ++++ | ++++ | ++++ | ++++ |
| Thiobacillus versutus | ATCC25364 | " | ++++ | ++++ | ++++ | ++++ |
| Desulfovibrio desulfuricans | ATCC 7757 | delta | ++++ | ++++ | ++++ | ++++ |
| Cardiobacterium hominis | GT2095 | Gm − | ++++ | ++++ | ++++ | ++++ |
| Francisella tularensis | GT2172 | Gm − | ++++ | − | ++++ | ++++ |
| Campylobacter jejuni | GT0022 | Campy | ++++ | ++++ | ++++ | ++++ |
| Campylobacter pylori | GT0026 | " | ++++ | ++++ | ++++ | ++++ |
| Campylobacter sputorum | GT0027 | " | ++++ | ++++ | ++++ | ++++ |
| Bacillus brevis | GT0803 | lowG+C | ++++ | ++++ | ++++ | ++++ |
| Bacillus subtilis | GT0804 | Gm + | ++++ | ++++ | ++++ | ++++ |
| Clostridium clostridioforme | ATCC25537 | " | ++++ | ++++ | ++++ | ++++ |
| Clostridium sordellii | GT0567 | " | ++++ | ++++ | ++++ | ++++ |
| Clostridium sporogenes | ATCC 3587 | " | ++++ | ++++ | ++++ | ++++ |
| Clostridium histolyticum | ATCC19401 | " | ++++ | ++++ | ++++ | ++++ |
| Clostridium perfringens | ATCC13124 | " | ++++ | ++++ | ++++ | ++++ |
| Clostridium ramosum | ATCC25582 | " | ++++ | ++++ | ++++ | ++++ |
| Kurthia zopfii | ATCC33403 | " | ++++ | ++++ | ++++ | ++++ |
| Lactobacillus acidophilus | GT0256 | " | ++++ | ++++ | ++++ | ++++ |
| Lactobacillus plantarum | GT0258 | " | ++++ | ++++ | ++++ | ++++ |
| Listeria monocytogenes | IG3299 | " | ++++ | ++++ | ++++ | ++++ |

\* Inclusivity and Exclusivity data was determined after overnight exposures.
\*\* Each organism is represented by 100 ng of CsTFA purified RNA.
\*\*\* Probe 1738 - hybridizations and washes were carried out at 37 C. ++++ = positive control level of hybridization, + = barely detectable and − = zero, ND = not done.

TABLE 4
DOT BLOT HYBRIDIZATION OF 23S rRNA-TARGETED PROBES

| Genus species | strain | div | PROBE HYBRIDIZATION | | | | | | |
|---|---|---|---|---|---|---|---|---|---|
| | | | 1730 | 1731 | 1658 | 1653 | 1654 | 1655 | 1651 |
| Acinetobacter calcoaceticus | GT0002 | Purple | ++++ | +++ | ++++ | ++++ | ++++ | ++++ | +++ |
| Aeromonas sobria | GT0007 | gamma | ++++ | ++++ | ++++ | +++ | ++++ | ++++ | − |
| Alteromonas putrefaciens | GT1945 | " | ++++ | +++ | ++++ | +++ | ++++ | ++++ | ++ |
| Citrobacter amalonaticus | GT0690 | " | ++++ | +++ | ++++ | +++ | ++++ | ++++ | +++ |
| Citrobacter diversus | GT0030 | " | ++++ | +++ | ++ | ++++ | ++++ | ++++ | ++ |
| Citrobacter freundii | GT0687 | " | ++++ | ++++ | ++++ | +++ | ++++ | ++++ | ++ |
| Edwardsiella tarda | GT0569 | " | ++++ | ++++ | ++++ | ++++ | ++++ | ++++ | ++++ |
| Enterobacter agglomerans | GT0683 | " | +++ | +++ | ++++ | ++++ | ++++ | ++++ | ++ |
| Enterobacter cloacae | GT0686 | " | ++++ | ++++ | ++++ | ++++ | ++++ | ++++ | +++ |
| Enterobacter sakazakii | GT0062 | " | +++ | ++ | ++++ | ++++ | ++++ | ++++ | ++ |
| Escherichia coli | GT1665 | " | ++++ | +++ | ++++ | ++++ | ++++ | ++++ | +++ |
| Escherichia coli | GT1592 | " | ++++ | ++++ | ++++ | ++++ | ++++ | ++++ | ++++ |
| Escherichia coli | GT1659 | " | ++ | ++ | ++ | ++++ | +++ | − | ++++ |
| Haemophilus influenza | GT0244 | " | +++ | + | ++ | ++ | ++ | − | ++++ |
| Haemophilus influenza | ATCC33391 | " | ND | ND | ND | ND | ND | ND | ND |
| Haemophilus ducreyi | GT0243 | " | ++++ | ++++ | ++++ | ++++ | ++++ | ++++ | ++++ |
| Hafnia alvei | GT0241 | " | ++++ | ++++ | ++++ | ++++ | ++++ | ++++ | ++ |
| Morganella morganii | GT0303 | " | ++++ | ++++ | ++++ | ++++ | ++++ | ++++ | ++ |
| Klebsiella pneumoniae | GT1500 | " | ++++ | ++++ | ++++ | ++++ | ++++ | ++++ | +++ |
| Proteus mirabilis | GT1496 | " | ++++ | ++++ | ++++ | ++++ | ++++ | ++++ | ++++ |
| Providencia alcalifaciens | GT0371 | " | ++++ | ++++ | ++++ | ++++ | ++++ | ++++ | ++++ |
| Pseudomonas aeruginosa | GT1909 | " | ++++ | ++++ | ++ | ++++ | ++++ | ++++ | +++ |
| Salmonella arizona | GT0799 | " | ++++ | +++ | ++++ | ++++ | +++ | ++++ | +++ |
| Salmonella typhimurium | GT0389 | " | +++ | +++ | ++++ | ++++ | +++ | ++++ | +++ |
| Serratia marcescens | GT0392 | " | ++++ | ++++ | ++++ | ++++ | +++ | ++++ | ++++ |
| Shigella flexneri | GT0798 | " | ++++ | ++++ | ++++ | +++ | +++ | ++++ | ++++ |
| Vibrio parahaemolyticus | GT0568 | " | ++++ | ++++ | ++++ | +++ | +++ | ++++ | ++ |
| Xanthomonas maltophilia | GT0417 | " | ++++ | ++++ | ++++ | +++ | +++ | − | +++ |
| Yersinia enterocolitica | GT0419 | " | ++++ | ++++ | ++++ | ++++ | +++ | ++++ | +++ |
| Alcaligines faecalis | GT0610 | Purple | +++ | +++ | + | − | +++ | ++++ | ++ |
| Branhamella catarrhalis | GT0014 | beta | +++ | +++ | ++++ | ++++ | +++ | ++++ | ++++ |
| Chromobacterium violaceum | GT2022 | " | ++++ | ++++ | ++++ | − | +++ | ++++ | +++ |
| Kingella indologenes | 0246 | " | ++++ | +++ | +++ | ++ | ++ | ++++ | + |
| Moraxella osloensis | GT0301 | " | ++++ | ++++ | ++++ | ++++ | +++ | ++++ | ++ |
| Morexella phenylpyruvica | GT0302 | " | +++ | +++ | + | ++++ | +++ | ++++ | ++++ |
| Neisseria gonorrhoeae | GT0315 | " | +++ | +++ | ++++ | − | ++++ | ++++ | + |
| Neisseria meningitidis | GT0349 | " | ++++ | ++++ | ++++ | − | +++ | ++++ | ++++ |
| Pseudomonas acidovorans | GT0376 | " | ++++ | ++++ | ++++ | − | +++ | ++++ | ++++ |
| Pseudomonas cepacia | GT2015 | " | ++++ | +++ | +++ | − | − | ++ | − |
| Rhodocyclus gelatinosa | ATCC17013 | " | +++ | +++ | +++ | − | ++ | − | ++ |
| Vitreoscilla stercoraria | | " | ++++ | ++++ | +++ | − | +++ | +++ | +++ |
| Achromobacter xerosis | GT0810 | Purple | +++ | +++ | +++ | − | − | ++ | +++ |
| Acidiphilium cryptum | ATCC33463 | alpha | + | − | ++ | − | − | − | +++ |
| Agrobacterium tumefaciens | GT2021 | " | ++ | ++ | ++++ | − | − | − | +++ |
| Brucella abortus | ATCC23448 | " | ++++ | ++++ | ++++ | − | − | − | ++++ |
| Flavobacterium capsulatum | GT2025 | " | +++ | +++ | ++++ | − | − | − | +++ |
| Mycoplana bullata | GT2023 | " | ++++ | +++ | + | − | − | − | − |
| Pseudomonas diminuta | GT2020 | " | +++ | +++ | + | − | − | − | − |

TABLE 4-continued
DOT BLOT HYBRIDIZATION OF 23S rRNA-TARGETED PROBES

| Organism | ID | Group | | | | | | | |
|---|---|---|---|---|---|---|---|---|---|
| *Rhodobacter sphaeroides* | ATCC17023 | " | ++++ | ++++ | ++++ | − | − | − | ++++ |
| *Rhodospirillum rubrum* | ATCC25903 | " | ++++ | ++++ | ++++ | ++++ | ++++ | − | ++++ |
| *Thiobacillus versutus* | ATCC25364 | " | ++++ | ++++ | +++ | − | − | − | +++ |
| *Desulfovibrio desulfuricans* | ATCC 7757 | delta | +++ | + | ++ | + | +++ | − | +++ |
| *Cardiobacterium hominis* | GT2095 | Gm − | +++ | +++ | − | − | +++ | − | + |
| *Francisella tularensis* | GT2172 | Gm − | ++++ | ++++ | ++++ | − | − | − | ++ |
| *Campylobacter jejuni* | GT0022 | Campy | +++ | + | ++++ | − | − | − | − |
| *Campylobacter pylori* | GT0026 | " | ++ | ++ | ++++ | − | − | − | +++ |
| *Campylobacter sputorum* | GT0027 | " | +++ | ++ | ++++ | − | − | − | − |
| *Bacillus brevis* | GT0803 | lowG+C | +++ | +++ | ++++ | ++++ | ++++ | ++++ | ++++ |
| *Bacillus subtilis* | GT0804 | Gm + | +++ | +++ | ++++ | ++++ | ++++ | ++++ | ++++ |
| *Clostridium clostridioforme* | ATCC25537 | " | − | − | + | ++++ | ++++ | ++++ | ++++ |
| *Clostridium sordellii* | GT0567 | " | ++++ | ++++ | ++++ | ++++ | ++++ | ++++ | +++ |
| *Clostridium sporogenes* | ATCC 3587 | " | +++ | +++ | ++++ | ++++ | ++++ | ++++ | ++++ |
| *Clostridium histolyticum* | ATCC19401 | " | ++++ | ++ | +++ | +++ | ++++ | ++ | +++ |
| *Clostridium perfringens* | ATCC13124 | " | ++++ | +++ | +++ | − | ++++ | − | ++++ |
| *Clostridium ramosum* | ATCC25582 | " | ++++ | +++ | − | − | − | − | ++++ |
| *Kurthia zopfii* | ATCC33403 | " | ++++ | ++++ | +++ | ++++ | ++++ | +++ | +++ |
| *Lactobacillus acidophilus* | GT0256 | " | +++ | +++ | − | + | ++++ | − | ++++ |
| *Lactobacillus plantarum* | GT0258 | " | ++++ | +++ | +++ | ++++ | ++++ | +++ | +++ |
| *Listeria monocytogenes* | IG3299 | " | ++++ | +++ | ++++ | ++++ | ++++ | +++ | +++ |
| *Mycoplasma pneumoniae* | ATCC15531 | " | +++ | ++ | +++ | − | − | − | − |
| *Mycoplasma putrefaciens* | ATCC15718 | " | +++ | ++ | ++ | − | − | − | − |
| *Peptostreptococcus productus* | ATCC27340 | " | − | − | ++ | ++++ | ++++ | ++++ | ++++ |
| *Planococcus citreus* | ATCC14404 | " | +++ | +++ | ++++ | ++++ | ++++ | +++ | +++ |
| *Staphlyococcus aureus* | GT0399 | " | ++++ | ++++ | ++++ | ++++ | ++++ | +++ | ++++ |
| *Staphylococcus aureus* | GT1711 | " | ++++ | ++++ | ++++ | ++++ | ++++ | +++ | +++ |
| *Staphylococcus epidermidis* | GT0401 | " | ++++ | ++++ | ++++ | +++ | ++++ | +++ | ++++ |
| *Staphylococcus haemolyticus* | ATCC29970 | " | ++++ | ++++ | ++++ | ++++ | ++++ | +++ | ++++ |
| *Streptococcus agalactiae* | GT0405 | " | +++ | +++ | − | ++++ | ++++ | +++ | ++++ |
| *Streptococcus bovis* | GT0668 | " | ++++ | +++ | − | +++ | ++++ | +++ | ++++ |
| *Streptococcus faecalis* | GT0406 | " | ++++ | +++ | +++ | ++++ | ++++ | +++ | +++ |
| *Streptococcus morbillorum* | GT2194 | " | +++ | ++ | +++ | ++++ | ++++ | +++ | +++ |
| *Streptococcus mutans* | GT0412 | " | +++ | ++ | − | ++++ | ++++ | +++ | +++ |
| *Streptococcus pneumoniae* | GT0408 | " | ++++ | +++ | − | +++ | ++++ | +++ | ++++ |
| *Streptococcus salivarius* | GT0410 | " | +++ | ++ | − | ++++ | ++++ | +++ | ++++ |
| *Streptococcus sanguis* | GT0411 | " | +++ | +++ | − | ++++ | ++++ | +++ | ++++ |
| *Bifidobacterium dentium* | GT0012 | hiG+C | +++ | +++ | − | − | − | − | ++++ |
| *Corynebacterium genitalium* | GT0045 | Gm + | +++ | +++ | +++ | ++++ | ++++ | ++ | ++++ |
| *Crynebacterium glutamicum* | GT2120 | " | ++++ | +++ | +++ | ++++ | ++++ | ++ | ++++ |
| *Corynebacterium pseudodiphtheriticum* | GT2119 | " | ++++ | ++++ | +++ | ++++ | ++++ | ++++ | ++++ |
| *Corynebacterium pseudotuberculosis* | GT2122 | " | ++++ | +++ | − | ++ | ++++ | ++ | ++++ |
| *Corynebacterium pyogenes* | GT2121 | " | + | − | ++ | ++++ | ++++ | +++ | +++ |
| *Corynebacterium xerosis* | GT0046 | " | − | − | + | ++++ | ++++ | ++ | +++ |
| *Mycobacterium bovis* | BCG | " | − | − | ++ | ++++ | ++++ | ++ | +++ |
| *Mycobacterium kansasii* | | " | + | − | +++ | ++++ | ++++ | +++ | ++++ |
| *Nocardia asteroides* | GT2191 | " | ++++ | ++++ | +++ | − | − | − | ++++ |
| *Rhodococcus rhodochrous* | | " | +++ | +++ | +++ | ++++ | +++ | ++ | ++++ |
| *Aerococcus viridans* | GT2116 | Misc | ++++ | ++++ | +++ | +++ | +++ | ++ | ++++ |
| *Fusobacterium necrophorum* | GT0238 | Gm + | ++++ | ++++ | − | +++ | +++ | + | − |
| *Fusobacterium prausnitzii* | ATCC27768 | " | +++ | − | ++ | ++ | +++ | − | ++++ |
| *Gemella haemolysans* | GT2118 | " | ++++ | ++++ | ++++ | ++ | ++++ | ++++ | ++++ |
| *Heliobacillus mobilis* | | " | +++ | ++ | ++++ | +++ | ++++ | ++++ | ++++ |
| *Phormidium ectocarpi* | | Cyano | + | ++ | − | +++ | ++++ | ++++ | − |
| *Plectonema boryanum* | | " | ++ | ++ | − | ++ | ++++ | +++ | − |
| *Borrelia burgdorferi* | | Spiro | +++ | ++ | ++ | − | − | − | +++ |
| *Borrelia turicatae* | | " | ++++ | +++ | ++++ | − | − | − | +++ |
| *Leptospira interrogans-pomona* | | " | +++ | ++ | ++++ | − | − | − | ++ |
| *Leptospira biflexa* (Patoc-Patoc) | | " | +++ | ++ | ++++ | − | − | − | ++++ |
| *Leptospira biflexa* (CDC) | | " | +++ | ++ | ++++ | − | − | − | ++++ |
| *Spirochaeta aurantia* | | " | ++++ | ++ | ++++ | − | − | − | ++++ |
| *Bacteroides fragilis* | 25285 | Bact | ++ | ++ | + | − | − | − | ++++ |
| *Bacteroides fragilis* | 29771 | " | ++ | ++ | + | − | − | − | ++++ |
| *Bacteroides thetaiotaomicron* | 0572 | " | + | + | + | − | − | − | ++++ |
| *Bacteroides melaninogenicus* | 0011 | " | − | − | + | ++ | ++ | − | ++++ |
| *Flavobacterium meningosepticum* | 0237 | " | + | − | + | − | − | − | +++ |
| *Chlamydia psittaci* | | Chlam | − | − | − | − | − | − | − |
| *Chlamydia trachomatis* | LGV | " | +++ | +++ | − | − | − | − | − |
| *Chlorobium limicola* | | Misc. | ++++ | +++ | + | ++++ | ++++ | +++ | +++ |
| *Chloroflexus aurantiacus* | Y400 | " | + | − | ++ | − | ++ | − | + |
| *Deinococcus radiodurans* | 2608 | " | ++++ | +++ | +++ | − | − | − | + |
| *Planctomyces maris* | 2577 | " | − | − | +++ | − | − | − | − |
| Normal Stool RNA | | | +++ | ++ | +++ | ++ | +++ | ++ | +++ |
| Mouse L-Cell | | | − | − | − | − | − | − | − |
| Wheat Germ | | | + | ++ | − | − | − | − | − |
| Normal Human Blood | | | − | − | − | − | − | − | − |
| *Candida lusitaniae* | 403-87 | | − | − | − | − | − | − | − |
| *Candida parapsilosis* | 882-88 | | − | − | − | − | − | − | − |
| *Candida tropicalis* | 224-87 | | − | − | − | − | − | − | − |

TABLE 4-continued
DOT BLOT HYBRIDIZATION OF 23S rRNA-TARGETED PROBES

| Genus species | strain | | | | | | | |
|---|---|---|---|---|---|---|---|---|
| Candida albicans | 1008-88 | − | − | − | − | − | − | − |
| Candida albicans | 223-87 | − | − | − | − | − | − | − |
| Candida albicans | 819-88 | − | − | − | − | − | − | − |

| | | | PROBE HYBRIDIZATION | | | | | | |
|---|---|---|---|---|---|---|---|---|---|
| Genus species | strain | div | 1512 | 1256 | 1398 | 1600 | 1601 | 1602 | 1596 | 1597 |
| Acinetobacter calcoaceticus | GT0002 | Purple | ++++ | ++++ | + | ++++ | ++++ | ++++ | ++++ | ++ |
| Aeromonas sobria | GT0007 | gamma | ++++ | ++++ | ++ | ++++ | ++++ | ++++ | ++++ | ++ |
| Alteromonas putrefaciens | GT1945 | " | ++++ | ++++ | ++ | ++++ | ++++ | ++++ | ++++ | +++ |
| Citrobacter amalonaticus | GT0690 | " | ++++ | +++ | + | ++++ | +++ | ++++ | +++ | +++ |
| Citrobacter diversus | GT0030 | " | ++++ | ++++ | + | ++++ | +++ | ++++ | +++ | +++ |
| Citrobacter freundii | GT0687 | " | ++++ | ++++ | + | ++++ | +++ | ++++ | +++ | ++++ |
| Edwardsiella tarda | GT0569 | " | ++++ | ++++ | + | ++++ | ++++ | ++++ | +++ | +++ |
| Enterobacter agglomerans | GT0683 | " | ++++ | ++++ | + | +++ | +++ | ++++ | +++ | ++ |
| Enterobacter cloacae | GT0686 | " | ++++ | ++++ | + | ++++ | +++ | ++++ | +++ | ++ |
| Enterobacter sakazakii | GT0062 | " | ++++ | ++++ | ++ | +++ | +++ | ++++ | +++ | ++ |
| Escherichia coli | GT1665 | " | ++++ | ++++ | + | +++ | +++ | ++++ | +++ | ++++ |
| Escherichia coli | GT1592 | " | ++++ | ++++ | + | ++++ | ++++ | ++++ | ++++ | ++++ |
| Escherichia coli | GT1659 | " | ++++ | +++ | + | +++ | ++ | ++++ | +++ | ++ |
| Haemophilus influenza | GT0244 | " | ++ | +++ | + | +++ | ++ | ++++ | +++ | ++ |
| Haemophilus influenza | ATCC33391 | " | ND | ND | ND | +++ | +++ | +++ | +++ | +++ |
| Haemophilus ducreyi | GT0243 | " | ++++ | ++++ | ++ | ND | ++ | ++++ | ++++ | ++ |
| Hafnia alvei | GT0241 | " | ++++ | ++++ | + | ++++ | +++ | ++++ | ++++ | +++ |
| Morganella morganii | GT0303 | " | ++++ | ++++ | + | ++++ | ++++ | ++++ | +++ | +++ |
| Klebsiella pneumoniae | GT1500 | " | ++++ | ++++ | + | ++++ | +++ | +++ | +++ | +++ |
| Proteus mirabilis | GT1496 | " | ++++ | ++++ | + | ++++ | ++++ | ++++ | +++ | +++ |
| Providencia alcalifaciens | GT0371 | " | ++++ | ++++ | + | ++++ | +++ | ++++ | +++ | +++ |
| Pseudomonas aeruginosa | GT1909 | " | ++++ | ++++ | ++ | ++++ | ++++ | ++++ | +++ | ++ |
| Salmonella arizona | GT0799 | " | ++++ | ++++ | + | ++++ | +++ | ++++ | +++ | ++ |
| Salmonella typhimurium | GT0389 | " | ++++ | ++++ | + | ++++ | +++ | ++++ | +++ | +++ |
| Serratia marcescens | GT0392 | " | ++++ | ++++ | + | ++++ | +++ | ++++ | +++ | ++ |
| Shigella flexneri | GT0798 | " | ++++ | ++++ | ++ | ++++ | ++++ | ++++ | ++++ | ++ |
| Vibrio parahaemolyticus | GT0568 | " | ++++ | +++ | ++ | +++ | +++ | ++++ | ++++ | ++ |
| Xanthomonas maltophilia | GT0417 | " | ++++ | +++ | ++ | ++++ | ++ | ++++ | ++++ | ++ |
| Yersinia enterocolitica | GT0419 | " | ++++ | ++++ | ++ | ++++ | ++++ | ++++ | ++++ | ++++ |
| Alcaligenes faecalis | GT0610 | Purple | ++++ | +++ | + | +++ | + | +++ | +++ | ++ |
| Branhamella catarrhalis | GT0014 | beta | ++++ | +++ | + | ++++ | ++ | +++ | +++ | +++ |
| Chromobacterium violaceum | GT2022 | " | ++++ | ++++ | + | ++++ | ++++ | +++ | +++ | +++ |
| Kingella indologenes | 0246 | " | ++++ | ++ | + | +++ | +++ | +++ | +++ | ++ |
| Moraxella osloensis | GT0301 | " | ++++ | +++ | + | ++++ | +++ | ++++ | +++ | +++ |
| Morexella phenylpyruvica | GT0302 | " | ++++ | ++++ | + | ++++ | ++ | +++ | +++ | +++ |
| Neisseria gonorrhoeae | GT0315 | " | ++++ | ++++ | + | ++++ | ++ | ++++ | ++++ | ++ |
| Neisseria meningitidis | GT0349 | " | ++++ | ++++ | + | ++++ | +++ | ++++ | ++++ | ++ |
| Pseudomonas acidovorans | GT0376 | " | ++++ | ++++ | + | ++++ | +++ | ++++ | ++++ | ++ |
| Pseudomonas cepacia | GT2015 | " | ++++ | +++ | + | ++++ | +++ | ++++ | +++ | ++ |
| Rhodocyclus gelatinosa | ATCC17013 | " | ++++ | +++ | + | +++ | +++ | ++++ | +++ | ++ |
| Vitreoscilla stercoraria | | " | ++++ | ++ | + | ++++ | +++ | ++++ | ++++ | ++++ |
| Achromobacter xerosis | GT0810 | Purple | ++++ | ++ | + | +++ | +++ | ++++ | +++ | +++ |
| Acidiphilium cryptum | ATCC33463 | alpha | ++++ | ++ | + | ++++ | +++ | ++++ | ++++ | ++++ |
| Agrobacterium tumefaciens | GT2021 | " | ++++ | ++ | + | ++ | ++ | ++++ | ++ | +++ |
| Brucella abortus | ATCC23448 | " | ++++ | ++++ | + | +++ | +++ | ++++ | +++ | +++ |
| Flavobacterium capsulatum | GT2025 | " | ++++ | +++ | + | ++++ | +++ | ++++ | ++ | +++ |
| Mycoplana bullata | GT2023 | " | ++++ | +++ | + | ++++ | +++ | ++++ | +++ | ++++ |
| Pseudomonas diminuta | GT2020 | " | ++++ | +++ | + | ++++ | +++ | ++++ | +++ | +++ |
| Rhodobacter sphaeroides | ATCC17023 | " | ++++ | +++ | ++ | ++++ | +++ | ++++ | +++ | +++ |
| Rhodospirillum rubrum | ATCC25903 | " | ++++ | ++++ | + | ++++ | +++ | ++++ | +++ | +++ |
| Thiobacillus versutus | ATCC25364 | " | ++++ | +++ | + | ++++ | ++++ | ++++ | ++++ | ++++ |
| Desulfovibrio desulfuricans | ATCC 7757 | delta | ++++ | +++ | + | ++++ | ++++ | ++++ | + | + |
| Cardiobacterium hominis | GT2095 | Gm − | ++++ | +++ | + | ++++ | +++ | ++++ | ++ | +++ |
| Francisella tularensis | GT2172 | Gm − | ++++ | +++ | + | ++++ | +++ | ++++ | ++++ | ++++ |
| Campylobacter jejuni | GT0022 | Campy | ++++ | − | ++++ | +++ | ++ | ++++ | +++ | +++ |
| Campylobacter pylori | GT0026 | " | ++++ | − | +++ | ++++ | +++ | ++++ | +++ | +++ |
| Campylobacter | GT0027 | " | ++++ | − | +++ | ++++ | +++ | ++++ | +++ | +++ |

TABLE 4-continued

DOT BLOT HYBRIDIZATION OF 23S rRNA-TARGETED PROBES

| Species | Strain | Group | | | | | | | | |
|---|---|---|---|---|---|---|---|---|---|---|
| sputorum | | | | | | | | | | |
| Bacillus brevis | GT0803 | lowG+C | ++++ | +++ | + | ++++ | +++ | ++++ | +++ | +++ |
| Bacillus subtilis | GT0804 | Gm+ | ++++ | +++ | + | ++++ | +++ | ++++ | ++++ | +++ |
| Clostridium clostridioforme | ATCC25537 | " | ++++ | +++ | + | +++ | ++ | ++++ | ++++ | +++ |
| Clostridium sordellii | GT0567 | " | ++++ | +++ | + | +++ | +++ | ++++ | ++++ | +++ |
| Clostridium sporogenes | ATCC 3587 | " | ++++ | +++ | + | +++ | ++ | ++++ | ++++ | +++ |
| Clostridium histolyticum | ATCC19401 | " | ++++ | +++ | + | − | + | ++++ | ++++ | ++ |
| Clostridium perfringens | ATCC13124 | " | ++++ | − | + | +++ | +++ | ++++ | ++++ | ++ |
| Clostridium ramosum | ATCC25582 | " | ++++ | − | + | ++ | ++ | ++++ | ++++ | ++ |
| Kurthia zopfii | ATCC33403 | " | ++++ | ++++ | + | ++++ | +++ | ++++ | ++++ | ++ |
| Lactobacillus acidophilus | GT0256 | " | ++++ | +++ | + | ++++ | +++ | ++++ | ++++ | +++ |
| Lactobacillus plantarum | GT0258 | " | ++++ | +++ | + | ++++ | +++ | ++++ | +++ | ++ |
| Listeria monocytogenes | IG3299 | " | ++++ | +++ | + | ++++ | +++ | ++++ | ++ | ++++ |
| Mycoplasma pneumoniae | ATCC15531 | " | ++++ | − | + | ++ | − | − | − | − |
| Mycoplasma putrefaciens | ATCC15718 | " | ++++ | − | − | +++ | ++ | ++++ | +++ | +++ |
| Peptostreptococcus productus | ATCC27340 | " | ++++ | +++ | − | ++ | ++ | ++++ | +++ | +++ |
| Planococcus citreus | ATCC14404 | " | ++++ | +++ | + | ++++ | +++ | ++++ | ++++ | +++ |
| Staphylococcus aureus | GT0399 | " | ++++ | ++++ | + | ++++ | +++ | ++++ | ++++ | +++ |
| Staphylococcus aureus | GT1711 | " | ++++ | +++ | + | ++++ | +++ | ++++ | +++ | +++ |
| Staphylococcus epidermidis | GT0401 | " | ++++ | +++ | + | ++++ | +++ | ++++ | +++ | +++ |
| Staphylococcus haemolyticus | ATCC29970 | " | ++++ | +++ | + | ++++ | +++ | ++++ | +++ | +++ |
| Streptococcus agalactiae | GT0405 | " | ++++ | +++ | + | ++++ | +++ | ++++ | +++ | ++++ |
| Streptococcus bovis | GT0668 | " | ++++ | ++ | + | ++++ | +++ | ++++ | +++ | ++++ |
| Streptococcus faecalis | GT0406 | " | ++++ | ++ | + | ++++ | +++ | ++++ | +++ | +++ |
| Streptococcus morbillorum | GT2194 | " | ++++ | +++ | + | ++ | +++ | ++++ | ++ | ++++ |
| Streptococcus mutans | GT0412 | " | ++++ | +++ | + | ++++ | ++ | ++++ | +++ | +++ |
| Streptococcus pneumoniae | GT0408 | " | ++++ | +++ | + | ++++ | ++ | ++++ | +++ | +++ |
| Streptococcus salivarius | GT0410 | " | ++++ | +++ | + | ++++ | ++ | ++++ | +++ | ++ |
| Streptococcus sanguis | GT0411 | " | ND | ND | + | ++++ | +++ | ++++ | +++ | +++ |
| Bifidobacterium dentium | GT0012 | hiG+C | − | +++ | + | ++++ | +++ | ++++ | +++ | +++ |
| Corynebacterium genitalium | GT0045 | Gm+ | ++ | +++ | + | ++++ | +++ | ++++ | ++++ | +++ |
| Crynebacterium glutanicum | GT2120 | " | ++ | +++ | + | ++++ | +++ | ++++ | ++++ | +++ |
| Corynebacterium pseudodiphtheriticum | GT2119 | " | ++++ | +++ | + | ++++ | +++ | ++++ | ++++ | +++ |
| Corynebacterium pseudotuberculosis | GT2122 | " | ++++ | +++ | + | ++++ | +++ | ++++ | ++++ | ++++ |
| Corynebacterium pyogenes | GT2121 | " | ++ | ++ | + | ++++ | ++ | ++++ | ++++ | ++++ |
| Corynebacterium xerosis | GT0046 | " | + | ++ | + | +++ | ++ | ++++ | ++ | +++ |
| Mycobacterium bovis | BCG | " | + | ++ | + | +++ | + | ++++ | ++ | +++ |
| Mycobacterium kansasii | | " | +++ | +++ | + | ++++ | +++ | ++++ | +++ | +++ |
| Nocardia asteroides | GT2191 | " | ++++ | +++ | + | ++++ | +++ | ++++ | ++++ | +++ |
| Rhodococcus rhodochrous | | " | ++ | +++ | + | ++++ | ++ | ++++ | ++++ | +++ |
| Aerococcus viridans | GT2116 | Misc | ++++ | +++ | + | ++++ | ++ | ++++ | ++++ | ++++ |
| Fusobacterium necrophorum | GT0238 | Gm+ | ++ | +++ | + | +++ | ++ | ++++ | ++++ | ++++ |
| Fusobacterium prausnitzii | ATCC27768 | " | ++++ | +++ | + | ++++ | +++ | ++++ | ++++ | ++++ |
| Gemella haemolysans | GT2118 | " | ++++ | + | + | ++++ | +++ | ++++ | ++++ | ++++ |
| Heliobacillus mobilis | | " | ++++ | +++ | + | − | + | ++++ | ++ | ++++ |
| Phormidium ectocarpi | | Cyano | ++++ | +++ | + | + | ++ | ++++ | ++ | ++ |
| Plectonema boryanum | " | | ++++ | +++ | + | + | + | ++++ | ++ | ++ |
| Borrelia burgdorferi | | Spiro | ++++ | +++ | + | +++ | +++ | ++++ | +++ | ++ |
| Borrelia turicatae | | " | ++++ | ++++ | + | ++++ | ++++ | ++++ | ++++ | ++ |
| Leptospira interrogans-pomona | | " | ++++ | +++ | + | +++ | +++ | ++++ | +++ | +++ |
| Leptospira biflexa (Patoc-Patoc) | | " | ++++ | +++ | + | +++ | ++ | ++++ | ++ | ++ |
| Leptospira biflexa (CDC) | | " | ++++ | +++ | + | +++ | ++ | ++++ | ++ | ++ |
| Spirochaeta aurantia | | " | ++++ | ++++ | + | +++ | ++++ | ++++ | ++ | ++ |
| Bacteroides fragilis | 25285 | Bact | ++++ | +++ | + | +++ | ++ | ++++ | ++ | ++ |

TABLE 4-continued
DOT BLOT HYBRIDIZATION OF 23S rRNA-TARGETED PROBES

| | | | | | | | | | | |
|---|---|---|---|---|---|---|---|---|---|---|
| Bacteroides fragilis | 29771 | " | ++++ | +++ | + | +++ | ++ | ++++ | +++ | ++ |
| Bacteroides thetaiotaomicron | 0572 | " | ++++ | +++ | + | + | + | ++++ | ++ | ++ |
| Bacteroides melaninogenicus | 0011 | " | ++++ | +++ | + | + | ++ | ++++ | +++ | + |
| Flavobacterium meningosepticum | 0237 | " | ++++ | ++++ | + | ++++ | ++++ | ++++ | ++++ | + |
| Chlamydia psittaci | | Chlam | − | +++ | − | ++++ | ++++ | +++ | ++ | + |
| Chlamydia trachomatis | LGV | " | − | +++ | − | ++++ | +++ | ++++ | ++ | + |
| Chlorobium limicola | | Misc. | ++++ | ++++ | + | ++++ | ++++ | ++++ | + | ++ |
| Chloroflexus aurantiacus | Y400 | " | ++ | +++ | + | ++ | ++ | ++++ | ++ | ++ |
| Deinococcus radiodurans | 2608 | " | ++++ | ++++ | + | ++++ | ++++ | ++++ | + | ++ |
| Planctomyces maris | 2577 | " | ++++ | +++ | + | ++++ | ++++ | ++++ | +++ | − |
| Normal Stool RNA | | | ++++ | +++ | − | +++ | +++ | ++++ | ++ | ++ |
| Mouse L-Cell | | | − | − | − | − | − | − | − | − |
| Wheat Germ | | | − | − | − | − | − | − | − | − |
| Normal Human Blood | | | − | − | − | − | − | − | − | − |
| Candida lusitaniae | 403-87 | | + | − | − | − | − | − | − | − |
| Candida parapsilosis | 882-88 | | + | − | − | − | − | − | − | − |
| Candida tropicalis | 224-87 | | + | − | − | − | − | − | − | − |
| Candida albicans | 1008-88 | | + | − | − | − | − | − | − | − |
| Candida albicans | 223-87 | | + | − | − | − | − | − | − | − |
| Candida albicans | 819-88 | | + | − | − | − | − | − | − | − |

\* Inclusivity and Exclusivity data was detetermined after overnight exposures.
\*\* Each organism is represented by 100 ng of CsTFA purified RNA. ++++ = positive level of hybridization, + = barely detectable and − = zero, ND = not done.

TABLE 5
DOT BLOT HYBRIDIZATION - GRAM POSITIVE & GRAM NEGATIVE PROBES

| | | | PROBE HYBRIDIZATION | | | | | | | |
|---|---|---|---|---|---|---|---|---|---|---|
| | | | 16S RNA-TARGET | | | 23S RNA-TARGET | | | | |
| Genus species | strain | div | 1744 | 1745 | 1746 | 1657 | 1656 | 1598 | 1599 | 1595 |
| Acinetobacter calcoaceticus | GT0002 | Purple | − | − | − | ++++ | − | ++ | − | ++++ |
| Aeromonas sobria | GT0007 | gamma | − | − | − | ++++ | − | ++ | + | ++++ |
| Alteromonas putrefaciens | GT1945 | " | − | − | − | ++++ | − | ++++ | − | ++++ |
| Citrobacter amalonaticus | GT0690 | " | − | − | − | ++++ | − | ++++ | − | ++++ |
| Citrobacter diversus | GT0030 | " | − | − | − | ++++ | − | ++++ | − | ++++ |
| Citrobacter freundii | GT0687 | " | − | − | − | ++++ | − | ++++ | − | ++++ |
| Edwardsiella tarda | GT0569 | " | − | − | − | ++++ | − | ++++ | − | ++++ |
| Enterobacter agglomerans | GT0683 | " | − | − | − | ++++ | − | ++ | − | ++++ |
| Enterobacter cloacae | GT0686 | " | + | + | − | ++++ | − | ++ | + | ++++ |
| Enterobacter sakazakii | GT0062 | " | − | − | − | ++++ | − | ++++ | − | ++++ |
| Escherichia coli | GT1665 | " | − | − | − | ++++ | − | ++++ | − | ++++ |
| Escherichia coli | GT1592 | " | − | − | − | ++++ | − | ++++ | − | ++++ |
| Escherichia coli | GT1659 | " | − | − | − | ++++ | + | ++ | + | ++++ |
| Haemophilus influenza | ATCC33391 | " | − | − | − | ++++ | − | ++++ | − | ++++ |
| Haemophilus ducreyi | GT0243 | " | − | − | − | ++++ | − | ++++ | + | ++++ |
| Hafnia alvei | GT0241 | " | − | − | − | ++++ | − | ++++ | − | +++ |
| Morganella morganii | GT0303 | " | − | − | − | ++++ | − | ++++ | − | +++ |
| Klebsiella pneumoniae | GT1500 | " | − | − | − | ++++ | − | ++++ | + | ++ |
| Proteus mirabilis | GT1496 | " | − | − | − | ++++ | − | ++ | + | +++ |
| Providencia alcalifaciens | GT0371 | " | − | − | − | ++++ | − | ++ | + | +++ |
| Pseudomonas aeruginosa | GT1909 | " | − | − | − | ++++ | − | ++ | + | ++++ |
| Salmonella arizona | GT0799 | " | − | − | − | ++++ | − | ++++ | + | ++++ |
| Salmonella typhimurium | GT0389 | " | − | − | − | ++++ | − | ++++ | − | ++++ |
| Serratia marcescens | GT0392 | " | − | − | − | ++++ | − | ++++ | − | +++ |
| Shigella flexneri | GT0798 | " | − | − | − | ++++ | − | ++++ | − | +++ |
| Vibrio parahaemolyticus | GT0568 | " | − | − | − | ++++ | − | ++++ | + | +++ |
| Xanthomonas maltophilia | GT0417 | " | − | − | − | + | + | ++++ | + | +++ |
| Yersinia enterocolitica | GT0419 | " | − | − | − | ++++ | − | ++++ | + | ++++ |
| Alcaligines faecalis | GT0610 | Purple | − | − | − | − | ++++ | ++++ | − | +++ |
| Branhamella catarrhalis | GT0014 | beta | − | − | − | ++++ | − | ++++ | − | +++ |
| Chromobacterium violaceum | GT2022 | " | − | − | − | ++++ | +++ | ++++ | + | +++ |
| Kingella indologenes | 0246 | " | − | − | − | ++++ | − | +++ | − | +++ |
| Moraxella osloensis | GT0301 | " | − | − | − | ++++ | − | ++++ | + | + |
| Morexella | GT0302 | " | − | − | − | ++++ | − | ++++ | − | ++++ |

TABLE 5-continued
DOT BLOT HYBRIDIZATION - GRAM POSITIVE & GRAM NEGATIVE PROBES

| | | | | | | | | | | |
|---|---|---|---|---|---|---|---|---|---|---|
| phenylpyruvica | | | | | | | | | | |
| Borrelia burgdorferi | | Spiro | − | + | +++ | − | ++++ | ++ | − | − |
| Borrelia turicatae | | " | − | ++ | ++++ | − | ++++ | ++++ | − | + |
| Leptospira interrogans-pomona | | " | − | + | − | − | ++++ | ++++ | ++ | + |
| Leptospira biflexa (Patoc-Patoc) | | " | − | − | − | − | ++++ | ++++ | ++ | + |
| Leptospira biflexa (CDC) | | " | − | − | − | − | ++++ | +++ | ++ | + |
| Spirochaeta aurantia | | " | ++++ | − | − | − | ++++ | ++ | ++++ | + |
| Bacteroides fragilis | 25285 | Bact | ++++ | − | − | − | − | − | ++++ | + |
| Bacteroides fragilis | 29771 | " | ++++ | − | − | − | − | − | ++++ | + |
| Bacteroides thetaiotaomicron | 0572 | " | + | − | − | − | − | − | ++++ | + |
| Bacteroides melaninogenicus | 0011 | " | ++++ | − | − | − | − | − | ++++ | + |
| Flavobacterium meningosepticum | 0237 | " | ++++ | − | − | − | + | − | +++ | − |
| Chlamydia psittaci | | Chlamy | − | − | − | − | − | + | + | ++ |
| Chlamydia trachomatis | LGV | " | − | − | − | − | − | ++ | ++ | ++ |
| Chlorobium limicola | | Misc. | ++++ | − | − | − | +++ | − | − | − |
| Chloroflexus aurantiacus | Y400 | " | ++++ | − | − | − | +++ | − | ++++ | +++ |
| Deinococcus radiodurans | 2608 | " | +++ | − | − | − | +++ | − | ++++ | + |
| Planctomyces maris | 2577 | " | − | − | − | − | − | − | − | − |
| Normal Stool RNA | | | +++ | ++++ | ++ | ++ | +++ | + | +++ | ++ |
| Mouse L-Cell | | | − | − | − | − | − | − | − | − |
| Wheat Germ | | | − | − | − | − | − | − | − | − |
| Normal Human Blood | | | − | − | − | − | − | − | − | − |
| Candida lusitaniae | 403-87 | | − | − | − | − | − | − | − | − |
| Candida parapsilosis | 882-88 | | − | − | − | − | − | − | − | − |
| Candida tropicalis | 224-87 | | − | − | − | − | − | − | − | − |
| Candida albicans | 1008-88 | | − | − | − | − | − | − | − | − |
| Candida albicans | 223-87 | | − | − | − | − | − | − | − | − |
| Candida albicans | 819-88 | | − | − | − | − | − | − | − | − |
| Mycoplasma pneumoniae | ATCC15531 | " | − | ++++ | ++++ | − | − | − | − | ++++ |
| Mycoplasma putrefaciens | ATCC15718 | " | − | ++++ | +++ | − | − | − | ++++ | − |
| Peptostreptococcus productus | ATCC27340 | " | ++++ | ++++ | ++++ | − | + | − | ++++ | − |
| Planococcus citreus | ATCC14404 | " | ++++ | ++++ | ++++ | − | ++++ | + | ++++ | − |
| Staphylococcus aureus | GT0399 | " | ++++ | ++++ | ++++ | − | ++++ | + | ++++ | − |
| Staphylococcus aureus | GT1711 | " | ++++ | ++++ | ++++ | − | ++++ | + | ++++ | − |
| Staphylococcus epidermidis | GT0401 | " | ++++ | ++++ | ++++ | − | ++++ | + | ++++ | − |
| Staphylococcus haemolyticus | ATCC29970 | " | ++++ | ++++ | ++++ | − | ++++ | + | ++++ | − |
| Streptococcus agalactiae | GT0405 | " | ++++ | ++++ | ++++ | − | ++++ | − | ++++ | − |
| Streptococcus bovis | GT0668 | " | ++++ | ++++ | ++++ | − | ++++ | − | ++++ | − |
| Streptococcus faecalis | GT0406 | " | ++++ | ++++ | ++++ | − | ++++ | − | ++++ | − |
| Streptococcus morbillorum | GT2194 | " | ++++ | ++++ | +++ | − | ++++ | + | ++++ | − |
| Streptococcus mutans | GT0412 | " | ++++ | ++++ | +++ | − | ++++ | − | ++++ | − |
| Streptococcus pneumoniae | GT0408 | " | ++++ | ++++ | ++++ | − | ++++ | − | ++++ | − |
| Streptococcus salivarius | GT0410 | " | ++++ | ++++ | ++++ | − | ++++ | − | ++++ | − |
| Streptococcus sanguis | GT0411 | " | ++++ | ++++ | ++++ | − | ++++ | − | ++++ | − |
| Bifidobacterium dentium | GT0012 | hiG+C | − | ++++ | +++ | ++++ | − | − | ++++ | + |
| Corynebacterium genitalium | GT0045 | Gm+ | ++++ | ++++ | ++++ | ++++ | + | − | ++++ | + |
| Crynebacterium glutanicum | GT2120 | " | ++++ | ++++ | ++++ | ++++ | − | − | ++++ | + |
| Corynebacterium pseudodiphtheriticum | GT2119 | " | ++++ | ++++ | ++++ | − | ++++ | + | ++++ | − |
| Corynebacterium pseudotuberculosis | GT2122 | " | ++++ | ++++ | ++++ | − | +++ | − | ++++ | − |
| Corynebacterium pyogenes | GT2121 | " | ++++ | ++++ | ++++ | − | − | + | ++++ | +++ |
| Corynebacterium xerosis | GT0046 | " | ++++ | ++++ | ++ | ++++ | − | − | ++++ | + |
| Mycobacterium bovis | BCG | " | ++++ | ++++ | − | ++++ | − | − | ++++ | + |
| Mycobacterium kansasii | | " | ++++ | ++++ | ++ | ++++ | − | − | ++++ | + |
| Nocardia asteroides | GT2191 | " | ++++ | − | − | − | − | ++++ | +++ | ++ |
| Rhodococcus rhodochrous | | " | ++++ | ++++ | + | ++++ | − | − | ++++ | + |
| Aerococcus viridans | GT2116 | Misc | ++++ | ++++ | ++++ | − | ++ | ++ | ++++ | − |

TABLE 5-continued

DOT BLOT HYBRIDIZATION - GRAM POSITIVE & GRAM NEGATIVE PROBES

| Organism | ID | Group | | | | | | | | |
|---|---|---|---|---|---|---|---|---|---|---|
| Fusobacterium necrophorum | GT0238 | Gm + | ++++ | ++++ | ++ | +++ | − | ++ | ++++ | − |
| Fusobacterium prausnitzii | ATCC27768 | " | ++++ | ++++ | ++ | ++ | − | + | ++++ | − |
| Gemella haemolysans | GT2118 | " | ++++ | ++++ | ++++ | − | ++++ | ++++ | ++++ | − |
| Heliobacillus mobilis | | " | ++++ | ++++ | +++ | − | ++++ | − | ++++ | − |
| Phormidium ectocarpi | | Cyano | ++++ | ++++ | ++ | − | − | − | ++++ | − |
| Plectonema boryanum | | " | ++++ | ++++ | − | − | + | − | ++++ | − |
| Neisseria gonorrhoeae | GT0315 | " | − | − | − | ++++ | ++++ | ++++ | − | ++++ |
| Neisseria meningitidis | GT0349 | " | − | − | − | ++++ | ++++ | ++++ | − | +++ |
| Pseudomonas acidovorans | GT0376 | " | − | − | − | ++++ | ++++ | ++++ | − | +++ |
| Pseudomonas cepacia | GT2015 | " | − | − | − | ++ | ++++ | ++++ | − | +++ |
| Rhodocyclus gelatinosa | ATCC17013 | " | − | − | − | − | − | ++++ | − | +++ |
| Vitreoscilla stercoraria | | " | − | − | − | − | ++++ | +++ | − | ++ |
| Achromobacter xerosis | GT0810 | Purple | − | − | − | ++++ | ++++ | ++++ | − | ++ |
| Acidiphilium cryptum | ATCC33463 | alpha | − | − | − | +++ | − | − | − | − |
| Agrobacterium tumefaciens | GT2021 | " | ++ | − | − | ++++ | − | ++++ | ++ | ++ |
| Brucella abortus | ATCC23448 | " | ++ | − | − | ++++ | − | ++++ | +++ | +++ |
| Flavobacterium capsulatum | GT2025 | " | + | − | − | ++++ | − | ++ | ++ | − |
| Mycoplana bullata | GT2023 | " | − | − | − | ++++ | − | ++ | − | − |
| Pseudomonas diminuta | GT2020 | " | − | − | − | ++++ | − | +++ | − | + |
| Rhodobacter sphaeroides | ATCC17023 | " | − | − | − | ++++ | − | +++ | − | ++ |
| Rhodospirillum rubrum | ATCC25903 | " | ++++ | − | − | ++++ | − | + | + | +++ |
| Thiobacillus versutus | ATCC25364 | " | ++ | − | − | ++++ | − | +++ | − | ++ |
| Desulfovibrio desulfuricans | ATCC 7757 | delta | − | − | − | − | − | +++ | − | ++ |
| Cardiobacterium hominis | GT2095 | Misc | − | − | − | ++++ | − | +++ | − | + |
| Francisella tularensis | GT2172 | Gm − | − | − | − | ++++ | − | +++ | − | ++++ |
| Campylobacter jejuni | GT0022 | Campy | − | − | − | − | ++++ | +++ | ++ | − |
| Campylobacter pylori | GT0026 | " | − | − | − | − | ++++ | ++++ | ++ | + |
| Campylobacter sputorum | GT0027 | " | − | − | − | − | ++ | ++++ | ++ | − |
| Bacillus brevis | GT0803 | lowG+C | ++++ | ++++ | ++++ | − | ++++ | + | ++++ | − |
| Bacillus subtilis | GT0804 | Gm + | ++++ | ++++ | ++++ | − | ++++ | + | ++++ | − |
| Clostridium clostridioforme | ATCC25537 | " | ++++ | ++++ | ++++ | − | ++++ | − | ++++ | − |
| Clostridium sordellii | GT0567 | " | ++++ | ++++ | ++++ | − | ++++ | − | ++++ | − |
| Clostridium sporogenes | ATCC 3587 | " | ++++ | ++++ | ++++ | − | ++++ | − | ++++ | − |
| Clostridium histolyticum | ATCC19401 | " | ++++ | ++++ | ++++ | − | ++++ | − | ++++ | − |
| Clostridium perfringens | ATCC13124 | " | ++++ | ++++ | ++++ | − | ++++ | − | ++++ | − |
| Clostridium ramosum | ATCC25582 | " | ++++ | ++++ | ++++ | − | − | − | ++++ | + |
| Kurthia zopfii | ATCC33403 | " | ++++ | ++++ | ++++ | − | ++++ | − | ++++ | − |
| Lactobacillus acidophilus | GT0256 | " | ++++ | ++++ | ++++ | − | +++ | − | ++++ | − |
| Lactobacillus plantarum | GT0258 | " | ++++ | ++++ | ++++ | − | +++ | + | ++++ | − |
| Listeria monocytogenes | IG3299 | " | ++++ | ++++ | ++++ | − | +++ | − | ++++ | − |

\* Inclusivity and Exclusivity data was determined after overnight exposures.
\*\* Each organism is represented by 100 ng of CsTFA purified RNA.
\*\*\* ++++ = positive level of hybridization, + = barely detectable and − = zero. Probe 1746 was hybridized at 37 C. and washes at 50 C.

What is claimed is:

1. A method of detecting the presence of eubacteria in a sample comprising:
   a) contacting said sample with at least one nucleic acid probe selected from the group of probes consisting of 1661, 1739, 1746, 1743, 1639, 1640, 1641, 1656, 1657, 1653, 1654, 1655, 1651, 1652, 1595, 1600, 1601, 1602, 1598, 1599, 1596, and 1597, under conditions that allow said probe to hybridize to rRNA or rDNA of said eubacteria, if present in said sample, to form hybrid nucleic acid complexes, which fragments do not form hybrids with rRNA or rDNA of mouse L cells, wheat germ, human blood, or Candida albicans; and
   b) detecting said hybrid nucleic acid complexes as an indication of the presence of said eubacteria in said sample.

2. The method of claim 1 wherein said eubacteria are gram-positive and said nucleic acid fragment is selected from the group of probes consisting of 1599, 1656, and 1746.

3. The method of claim 1 wherein said eubacteria are gram-negative and said nucleic acid fragment is selected from the group of probes consisting of 1599, 1656, and 1746.

* * * * *